United States Patent [19]
Vary

[11] Patent Number: 5,800,984
[45] Date of Patent: Sep. 1, 1998

[54] NUCLEIC ACID SEQUENCE DETECTION BY TRIPLE HELIX FORMATION AT PRIMER SITE IN AMPLIFICATION REACTIONS

[75] Inventor: Calvin P. H. Vary, Windham, Me.

[73] Assignee: Idexx Laboratories, Inc., Westbrook, Me.

[21] Appl. No.: 294,424

[22] Filed: Aug. 23, 1994

Related U.S. Application Data

[63] Continuation of Ser. No. 922, Jan. 6, 1993, abandoned, which is a continuation of Ser. No. 629,601, Dec. 17, 1990, abandoned.

[51] Int. Cl.$^6$ .............................. C12Q 1/68; C12Q 1/70; C12P 19/34; C07H 21/04
[52] U.S. Cl. .......................... 435/6; 435/91.1; 435/91.2; 536/24.3; 536/24.31; 536/24.32; 536/24.33
[58] Field of Search ...................... 435/6, 91.1, 91.2; 536/24.3, 27.1, 24.31, 24.33

[56] References Cited

U.S. PATENT DOCUMENTS

| | | | |
|---|---|---|---|
| 4,683,195 | 7/1987 | Mullis et al. | 435/91.2 |
| 4,767,699 | 8/1988 | Vary et al. | 435/6 |
| 4,882,269 | 11/1989 | Schneider et al. | 435/6 |
| 5,176,996 | 1/1993 | Hogan et al. | 435/6 |
| 5,422,251 | 6/1995 | Fresco | 435/91.1 |

FOREIGN PATENT DOCUMENTS

| | | |
|---|---|---|
| 0 375 408 | 6/1990 | European Pat. Off. . |
| WO 87/01730 | 3/1987 | WIPO . |
| WO 89/07149 | 8/1989 | WIPO . |
| WO 90/15884 | 12/1990 | WIPO . |
| WO 91/06626 | 5/1991 | WIPO . |

OTHER PUBLICATIONS

Takasugi et al, (Jul. 1991), "Sequence specific photo-induced crosslinking of the two strands of double helical DNA a psoralen covalently linked to a triple helix forming oligonucleotide", Proc. Natl. Acad. Sci. 88:5602–5606.
Cadieux et al, (1993), "Use of a triplex polymerase chain reaction for the detection and differentiation of *Mycoplasma pneumoniae* and *Mycoplasma genitalium* in the presence of human DNA", J. Gen. Microbiol. 139:2431–2437.
Matthews et al., Analytical Biochemistry, vol. 169, pp. 1–25, 1988.
P. Y. Wu and R. B. Wallace Genomics 4, 560–569 (1989).
G. Laszlo and H. B. Dickler Hybridoma 9, 111–117 (1990).
L. E. Morrison et al. Anal. Biochem. 183, 231–244 (1989).
P. D. Foglesong Anal. Biochem. 182, 284–288 (1989).
I. Laprenotte et al. J. Virol 50, 884–894 (1984).
L. Ratner et al. Nature 313, 277–284 (1985).
K. Seedorf et al. Virology 145, 181–185 (1985).
S. T. Cole and O. Danos J. Mol. Biol. 193, 599–608 (1987).
J. L. Hess et al. J. Virol. 60, 385–393 (1986).
Y. Ono et al. Nucl. Acids Res. 11, 1747–1757 (1983).
Francois et al., Nucleic Acids Research 16:11431–11440, 1988.
Kohwi et al., Proc. Natl. Acad. Sci. USA 85:3781–3785, 1988.
Cooney et al., Science 241:456, 1988.
Maher et al., Science 245:725, 1989.
Minton, J. of Exp. Path. 2:135, 1985.
Moser and Dervan, Science 238:645, 1987.
Francois et al., Proc. Natl. Acad. Sci. USA 86:9702, 1989.
Le Doan et al., Nucl. Acids Res. 15:7749, 1987.
Vlassov et al., Gene 72:313, 1988.
Hanvey et al., Nucl. Acids Res. 18:157, 1990.
Leubke and Dervan, Jour. of the Amer. Chem. Soc. 111:8733, 1989.
Baum, C&EN, Nov. 14, 1988.
Praseuth et al., Proc. Natl. Acad. Sci. USA 85:1349, 1988.
Povsic and Dervan, Jour. of the Amer. Chem. Soc. 111:3059, 1989.
Broitman et al., Proc. Natl. Acad. Sci. USA 84:5120, 1987.
Lipsett, J. Biol. Chem. 239:1256, 1964.
Griffin and Dervan, Science 245:967, 1989.
Morgan and Wells, J. Mol. Biol. 37:63, 1968.
Letai, Biochemistry 27:9108, 1988.
Sheffield et al., Proc. Nat. Acad. Sci. USA 86:232, 1989.
Christen and Montalbeno, J. of Cell. Biochem., Abstract WH117, Supp. 13E, 1989.
Harding et al., Nucl. Acids Res. 17:6947, 1989.
Wu et al., Proc. Natl. Acad. Sci. USA 86:2757, 1989.
Syvanen et al., Nucl. Acids Res. 16:11327, 1988.
Kemp et al., Proc. Nat. Acad. Sci. USA 86:2423, 1989.
Keller et al., Anal. Biochem. 177:27, 1989.
Kenten et al., publication of IGEN, Inc. Rockville, MD.
Kumar et al., AIDS Research and Human Retroviruses 5:345, 1989.

*Primary Examiner*—W. Gary Jones
*Assistant Examiner*—Jeffrey Fredman
*Attorney, Agent, or Firm*—Fish & Richardson P.C.

[57] ABSTRACT

Disclosed is a method for detecting a nucleic acid target sequence by formation of triple helix nucleic acid structures. The method may, but need not, involve amplifying the nucleic acid in vitro using cycles of denaturation and amplification to yield product duplexes, and detecting the product duplexes by hybridizing a third strand of nucleic acid to the product duplexes without denaturation. The triple helix-forming duplex sequences may be endogenous to the target sequence being detected, or they may be introduced in the probes used during amplification.

60 Claims, 8 Drawing Sheets

| GENBANK CODE | GENE |
|---|---|
| HUMGCB1 | EHuman glucocerebrosidase gene, complete cds. |
| HUMGASTA | EHuman gastrin gene, complete cds. |
| HUMGHCSA | EHuman growth hormone (GH-1 and GH-2) and chorionic |
| HUMFOLLI1 | EHuman follistatin gene, exons 1-5. |
| HUMRBA | EHuman retinoblastoma (pp110RB) gene, 5' flank. |
| HUMRASR2 | EHuman R-ras gene, exons 2 through 6. |
| HUMFOLLI2 | EHuman follistatin gene, exon 6. |
| HUMPKCB2A | EHuman mRNA for protein kinase C (PKC) type beta II |
| HUMGP5MOS | EHuman gene fragment related to oncogene c-mos with |
| HUMGSHPXG | EHuman gluthathione peroxidase gene, complete cds. |
| HUMARASR1 | EHuman R-ras gene, exon 1. |
| HUMPP15 | EHuman gene for PP15 (placental protein 15). |
| HUMPRCM | EHuman protein CmRNA, complete cds. |
| HUMCYPIIE | EHuman cytochroe P450IIE1 (ethanol-inducible) gene |
| HUMERP | EHuman erythropoietin gene, complete cds. |
| HUMCYCPSJ | EHuman somatic cytochrome c (HS11) processed pseudo |
| HUMFCERI | EHuman mRNA for high affinity IgE receptor alpha-su |
| HUMPLAP1A | EHuman placental alkaline phosphatase (PLAP-1) gene |
| HUMERPA | EHuman erythropoietin gene, complete cds. |
| HUMIFNIN3 | EHuman interferon-inducible mRNA fragment (cDNA 6-1 |
| HUMIFNB3 | EHuman interferon-beta-3 gene. |
| HUMMHDRR3 | EHuman MHC class II lymphocyte antigen DPw4-beta-2 |
| HUMIGHAD | EHuman Ig rearranged H-chain epsilon-3 pseudogene, |
| HUMMHDC3B | EHuman MHC class II HLA-DC-3beta gene (DR3,3). |
| HUMMRP8A | EHuman migration inhibitory factor-related protein |
| HUMHSC70 | EHuman hsc70 gene for 71 kd heat shock cognate prot |
| HUMMLVI2 | EHuman genomic Mlvi-2 locus with Alu insert. |
| HUMMPOA | EHuman myeloperoxidase gene, exons 1-4. |
| HUMKAL1 | EHuman glandular kallikrein gene, region 5' to the |
| HUMINSCR | EHuman insulin receptor (allele 1) gene, exons 14, |
| HUMKEREP | EHuman 50 kd type I epidermal keratin gene, complet |
| HUMKER18 | EHuman keratin 18 (K18) gene, complete cds. |
| HUMKERP2 | EHuman keratin pseudogene, exons 2-8. |
| HUMINCPPS | EHuman cysteine-pseudogene, inhibitor pseudogene (CS |
| HUMMHSXH | EHuman MHC class II HLA-SX-alpha gene. |
| HUMINSR | EHuman insulin receptor mRNA, complete cds. |
| HUMMAC1A | EHuman Mac-1 gene encoding complement receptor type |
| HUMP5311 | EHuman cellular phosphoprotein p53 gene, exon 11. |
| HUMHBBBP1 | EHuman beta-globin gene cluster, region homologous |
| HUMP13093 | EHuman mRNA for laukocyte adhesion glycoprotein p15 |
| HUMHBB | EHuman beta globin region on chromosome 11. |
| HUMHBB | EHuman beta globin region on chromosome 11. |
| HUMHBB51 | EHuman beta globin gene cluster extreme 5' flank: d |
| HUMHBB | EHuman beta globin region on chromosome 11. |
| HUMHOXB | EHuman homeo box c8 protein, mRNA, complete cds. |
| HUMNGLB | EHuman beta-nerve growth factor (beta-NGF) gene. |
| HUMMYCC | EHuman (Lawn) c-myr proto-oncogene, complete coding |

FIG. 8a

| GENBANK CODE | GENE |
|---|---|
| HUMMYCRT | EHuman (Raji) translocated t(8;14) c-myc uncogene, |
| HUMINSTRA | EHuman insulin receptor mRNA, complete cds. |
| HUMNMYCA | EHuman germ line n-myc gene. |
| HUMNMYC | EHuman N-myc gene. exons 8 and 3. |
| PIGPKCAMPA | EPig cAMP-dependent protein kinase catalytic alpha |
| PIGMHDRG | ESwine MHC class I PDE-glycoprotein mRNA, complete |
| RABBGLOB | ERabbit beta-like globin gene cluster encoding the |
| PIGFSA | EPig follistatin (FS) gene, complete cds. |
| RABBGLOB | ERabbit bata-like globin gene cluster encoding the |
| GOTHBBPS1 | EGoat beta-x-globin pseudogene with 3' flank. |
| BOVCOXPS | EBovine cytochrome c oxidase subunit IV processed p |
| DOGGPCR8 | EC.familiaris MRNA for G protein-coupled receptor, |
| RABMHDPA | ERabbit MHC class II DP alpha-1 gene (RLA K10 haplp |
| RABPHXC | ERabbit phosphatase X catalytic subunit mRNA, 3' en |
| PIGRELXA | EPorcine relaxin gene, complete cds. |
| BOVHMG1 | EBovine mRNA for high mobility group 1 (HMG1) prote |
| GOTHBBZPS | EGoat beta-z-globin pseudogene. |
| DOGGPCR1 | EC.familiaris mRNA for G protein-coupled receptor, |
| BOVTDTR | EBovine mRNA for terminal deoxynucleotidyltransfera |
| RABBGLOG | ERabbit beta-like globin gene cluster encoding ehr |
| RABBGLOB | ERabbit beta-like globin gene cluster encoding the |
| SHPCRFA | ESheep corticotropin releasing factor gene, complet |
| RABUTGLO5 | ERabbit uteroglobin gene 5'-flank EcoRI2-EcoRI3 fra |
| PIGAPOB2 | EPig apolipoprotein B gene (Lpb), exons 26 through |
| RABHBB1B1 | ERabbit beta1-globin gene (allele 2), complete cds |
| BOVPRCI3 | EBovine placental prolactin-ralated protein (bPRC-I |
| BOVTMD | EBovine thrombomodulin mRNA, 3' end. |
| PIGTFR | EPorcine transferring mRNA, 3' end. |
| RABRSCA | ERabbit short interspersed C repeat (SINE), about 1 |
| PININHBAR | EPorcine mRNA for inhibin beta (a)-subunit. |
| PIG2APHA | EPorcine protein phosphatase 2A alpha subunit mRNA, |
| BOVPGII | EBovine mRNA for bone proteoglycan II. |
| BOVATPS | EBovine mitochondrial ATP synthase gamma subunit ge |
| BOVMARCKS | EBovine 80-87 kd myrstoylated alanine-rich C kinas |
| DOGATPBR | EDog kidney mRNA for (Na+/K+)-ATPase beta-subunit. |
| RABSTROMR | ERabbit stromelysin gene, 5" flank. |
| GOTHBBEII | EGoat embryonic beta-globin epsilon-II complete gen |
| BOVPTHG | EBovine parathyroid hormone gene, complete coding r |
| BOVTHYR5 | EBovine thyroglobulin gene exon 18. |
| BOVGLYAA3 | EBovine pituitary glycoprotein hormone alpha-subuni |
| BOVKERVIC | EBovine epidermal cytokeratin VIb gene, complete cd |
| LEEBGLOB | ELepus europaeus adult beta-globin gene. |
| BOVPKC | EBovine beta type protein kinase CmRNA, complete c |
| BOVIRBP | EBovine interphotoreceptor retinoid-binding protein |
| RABDPG | ERabbit reticulocyte 2,3-bisphosphoglycerate (DPG) |
| BOVHBBE4 | EBovine epsilon-4 beta-globin gene, complete cds. |
| BOVHBP1 | EBovine beta-globin psl-1 pscudogene, complete cds. |
| BOVHBP2 | EBovine beta-globin psi-2 psurdogene, complete cds. |

FIG. 8b

| GENBAND CODE | GENE |
|---|---|
| CHKCPG | EChicken proteoglycan core protein n=gene lase 5 exo |
| CHKPPGA | EChicken processed pseudogene, complete cds. |
| CHKCPS1 | EChicken processed pseudogene CPS1 related to the r |
| CHKOVAL | Echicken ovalbumin gene including flanking sequence |
| CHKCRYAA | EChicken alpha-A-crystallin gene, complete cds and |
| CHKMYLCC | EChicken myosin alkali light chain (MLC1-f/MLC3-f) |
| CHKCG1A1 | EChicken pro-alpha-1 collagen(I) mRNA, 3'end. |
| CHKCERBA1 | EChicken c-erb A gene exon 1 and flanks. |
| CHKCG1A2 | EChicken type-1 collagen pro-alpha-2, exon 2 & 3. |
| CHKCMYCA | EChicken tumor 10 c-myc DNA, exons 2 ad 3. |
| CHKTGFB4 | EChicken mRNA for transforming growth factor-beta 4 |
| CHKMHC3 | EChicken embryonic myosin heavy chain (MHC) gene 3' |
| CHKMLC131 | EChicken fast myosin alkali light chain, exon 1 spe |
| CHKC1G | EChicken histone H1 gene, clone lambda-CHQ1. |
| CHKH2A | EChicken histone H2A gene. |
| CHKH234G | EChicken histone LH4, RH4, H3, LH2A and RH2A genes. |
| CHKH2A2B | EChicken histone H2A/H2B gene pair and flanks. |
| CHKMYHE | EChicken embryonic myosin heavy chain gene, complet |
| CHKCOACA | EChicken acetyl-CoA carboxylase mRNA, complete cds. |
| CHKCYP450 | EChicken cytochrome P-450 (phenobarbital-inducible) |
| CHKDYS | EChicken mRNA for dystrophin (Suchenne muscular dys |
| CHKMYHB | EChicken fast-white myosin heavy chain (adult isofo |
| XELH1PS1 | Exenopus laevi5 h1 histone pseudogene. |
| XELHI53LA | Exenopus laevi5 h3 histone mrna. |
| XEBACTA3 | EX.borealis cytoskeletal actin type 1 gene, exon 4. |
| XELCONNEX | EX.laevis connexin 38 mRNA, complete cds. |
| CHKC1PA1M | EChicken type-1 collagen pro-alpha-1 chain mRNA. |
| APTRDNA | EAscaphus truei ribosomal DNA intergenic spacer. |
| XELHX1H3 | EX.laevis histone H1B, H2A, H2B, and H4 genes, comp |
| XELSEKIIB | EX.laevis ribosomal protein S6 kinase II bata (SEKI |
| XELHX1H1 | EX.laevis histone H1B, H2A, H2B, and H4 genes, comp |
| DUKHGAP | EDuck embryonic alpha-globin pi' gene, complete cds. |
| DUKCRYD3A | EDuck delta-crystallin gene exon 3 fragment. |
| CHKTNC | EChicken troponin C (TNC) mRNA, complete cds. |
| CHKVITUP | EChicken vitellogenin gene upstream region (2kb). |
| CHKY | Echicken y gene, including flanking wequences. |
| DUKHBB | Educk beta-globin mrna. |
| CHKMYC | EChicken cellular myc proto-oncogene, complete cds. |
| DUKH5 | EDuck (Cairina moschata) H5 histone gene, complete |
| CHKTHD | EChicken thioredoxin protein, complete cds. |
| CHKLNKPG | EChicken cartilage link protein mRNA, complete cds. |
| CHKFASA | EChicken fatty acid synthase gene, 3' and. |
| RANFERPG | EFrog (Rans catesbelana) apoferritin pseudogene. |
| CHKFERH | EChicken ferritin H-subunit gene, complete cds. |
| DUKFASA | EDuck (A.platyrnynchos) S-acyl fatty acid synthase |
| CHKMLC138 | EChicken fast myosin alkali light chains, exons 1 a |
| ONGRAL1A | EOncnocer volvunus RAL-1 mRNA, complete cds. |
| OCTHEM | EO.dorlein memocyanin mRNA, 3' end. |
| TRBRGAB | ET.brucei trucei 5S ribosomal RNA gene, clone p5S-2 |

FIG. 8c

| GENBANK CODE | GENE |
|---|---|
| TRBRGAC | ET.brucei rhodesiense 5S ribosomal RNA gene, clone |
| DDIMYHC | ED.discoideum myosin heavy chain gene, complete cds |
| TRBRGAA | ET.brucei brucei 5S ribosomal RNA gene, clone p5S-1 |
| NEMRDNA2 | EAscaris bumbricoides rDNA with 18S rRNA 5' end. |
| DDIRAS | ESlime mold (D.discoideum) ras-homologous gene, com |
| DDIPSTCAT | EDictyostelium discoideum pst-cath gene encoding ps |
| DDIPYR56G | EDictyostelium discoideum DdPYR5-6 gene for UMP syn |
| DDIHPERB | ED.discoideum protein 23Cgene, 5' end. |
| DDIDIFIND | ED.discoideum DIF-inducible mRNA. |
| PFASA7 | EPlasdmodium falciparum (isolate NF7) S antigen gen |
| PFASA27 | EPlasmodium falciparum (isolate FC27) S-antigen gen |
| DDICYSPRO | ESlime mold (D.discoideum) cysteine proteinase 1 mR |
| DDIDG17A | EDictyostelium discoideum DG17 gene, complete cds. |
| DDIDRE1AC | ED.discoideum insertion elements DRE1a and DRE2-III |
| TRBRGAD | ET.brucei 5S ribosomal gene, complete cds. |
| DDIDOD | ESlime mold (D.discoideum) dihydroorotate dehydroge |
| DDIDISCIG | ESlime mold (D.discoideum) discoidin I-gamma gene, |
| DDIDISIA | ESlime mold (D.discoideum) discoidin-ia gene. |
| PBSCSP | EP.brasilianum circumsporozoite protein gene, 3'en |
| PFAP41R | EP.falciparum aldolase (P41) gene, complete cds. |
| SCMHGPRT | ES.mansoni hypoxanthine-guanine phosphoribosyltrans |
| DROTNF192 | ED.melanogaster transposable element F19, 3' juncti |
| PLMCSP | EP.malariae circumsporozoint protein gene, complete |
| PFARESAG1 | EP.falciparum FC27 RESA gene for ring-infected eryt |
| DROLAMB1 | ED.melanogaster laminin B1 subunit mRNA, complete c |
| DROORFI | EDrosophila DNA for hybridizing with human preproin |
| SUSHISPS3 | ESea urchin (S.purpuratus) early histone H2Bpseudo |
| DROGBR | ED.melanogaster glue gene cluster 68C boundary regi |
| DROH2AVD | ED. melanogaster H2AvD mRNA for histone 2A variant. |
| PFARESAR1 | EP.falciparum FC27 Ag46 RESA mRNA for ring-infected |
| DDITGVM | ED.discoideum Val-tRNA gene, clone lambda-ValGUU13. |
| DDITND312 | ESlime mold (D.discoldeum strain Ax-3L) transposons |
| NEM18SRN5 | EAscaris lumbricoldes 12S ribosomal DNA 5" region. |
| DDITGVF | ED.discoideum Val-tRNA gene, clone lambda-ValGUUB. |
| DDITGVH | ED.discoldeum val-tRNA gene, clone lambda-ValGUUB. |
| DROYP12 | ED.meianogaster yp1 and yp2 genes, encoding yolk pr |
| DROTPOD | EDrosophila DNA for transposable element D near 3'e |
| PFASERAA | EP.falciparum serine-repeat antigen protein gene (S |
| DDIUBIRPB | ESlime mold (S.discoikeum) ubiquitin lambda-229 gen |
| DDIUDPGP | ED.discoideum UDP glucose pyrophosphorylase gene, c |
| NEMRDNAI | EAscaris lumbricoides rDNA with 18S rRna gene 5'-en |
| PFAHRPC | EP.falciparum histidine-rich protein genes. |
| PFA412ANT | EP.falciparum 41-2 protein antigen, complete cds. |
| CHIRGNTS | EC.thummi piger non-transcribed spacer region of rR |
| PFACSP | EP.falciparum (Wellcome) circumsporocoite protein g |
| TRBVSG17B | Et.brucel viriant surface glycoprotein 117b mrna, S |
| DDIACT32 | ESlime mold (D.oiscoldeum) actin 6 gene, 3' end. |
| CHIBR1G | EChironomus pallidivittatus BR1 gene for giant secr |
| DDIACT15P | EDictyostelium actin 15 gene promoter region. |
| PFAACTA | ED.falciparum pf-actin I gene encoding actin, compl |
| PFAHPRT | EPlasmodium mRNA for hypoxanthine-guanine phosphori |

FIG. 8d

| GENBANK CODE | GENE |
|---|---|
| DDIACT15 | ED.discoideum actin 15 gene, complete cds. |
| PFAABRA | EPlasmodium falciparum p101/acidic basic repeat ant |
| TRCSLRCA | ET.cruzi small spliced leader (mini-exon) RNA gene |
| TRCSLRC | ETrypanosoma cruzi small spliced leader (mini-exon) |
| DDIACT24 | ESlime mold (D.discoideum) actin 2-sub 2 pseudogene |
| BRPANTP | EB.malayi 63 kg antigen (potentially protective) ge |
| TRCKAP | ET.cruzi kinetoplast-allociated protein (KAP) gene, |
| | EPlasmodium falciparum circumsporozoite (CS) protei |

FIG. 8e

SEQUENCE LISTING ( 1 ) GENERAL INFORMATION:

( i i i ) NUMBER OF SEQUENCES: 49

( 2 ) INFORMATION FOR SEQ ID NO: 1 :

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION:SEQ ID NO: 1 :

GGAAGGAAAG AAGGAG                                        16

( 2 ) INFORMATION FOR SEQ ID NO: 2 :

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION:SEQ ID NO: 2 :

CTCCTTCTTT CCTTCC         16

( 2 ) INFORMATION FOR SEQ ID NO: 3 :

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION:SEQ ID NO: 3 :

CCTTCCTTTC TTCCTC         16

( 2 ) INFORMATION FOR SEQ ID NO: 4 :

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION:SEQ ID NO: 4 :

CCCCTTTTTC TCTCCTTTCT CGGACAATGA CGGTTACGG         39

( 2 ) INFORMATION FOR SEQ ID NO: 5 :

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION:SEQ ID NO: 5 :

CCTCTCTTCT CTCTTCTCTC GGACAATGAC GGTTACGG         38

( 2 ) INFORMATION FOR SEQ ID NO: 6 :

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION:SEQ ID NO: 6 :

CCCCTTTTTC TCTCCTTTCT CCAAGGCGAT CAGCAACGCG G         41

( 2 ) INFORMATION FOR SEQ ID NO: 7 :

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION:SEQ ID NO: 7 :

CGGACAATGA CGGTTACGG         19

( 2 ) INFORMATION FOR SEQ ID NO: 8 :

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION:SEQ ID NO: 8 :

CAAGGCGATC AGCAACGCGG                                                                  20

( 2 ) INFORMATION FOR SEQ ID NO: 9 :

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION:SEQ ID NO: 9 :

CTCTTTCCTC TCTTTTTCCC C                                                             21

( 2 ) INFORMATION FOR SEQ ID NO: 10 :

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION:SEQ ID NO: 10 :

CTCTCTTCTC TCTTCTCTCC                                                              20

( 2 ) INFORMATION FOR SEQ ID NO: 11 :

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION:SEQ ID NO: 11 :

GCCCGCAACG CCGATACC                                                                 18

( 2 ) INFORMATION FOR SEQ ID NO: 12 :

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION:SEQ ID NO: 12 :

CCCAGGATGA CGCCGAAT                                                                 60

( 2 ) INFORMATION FOR SEQ ID NO: 13 :

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION:SEQ ID NO: 13 :

CCCCTTTTTC TCTCCTTTCT CGCCGCTAAC GCCCAACAC                          39

( 2 ) INFORMATION FOR SEQ ID NO: 14 :

( i ) SEQUENCE CHARACTERISTICS:
  ( A ) LENGTH: 36
  ( B ) TYPE: nucleic acid
  ( C ) STRANDEDNESS: single
  ( D ) TOPOLOGY: linear ( i i ) SEQUENCE DESCRIPTION:SEQ ID NO: 14 :

CCTCTCTTCT CTCTTCTCT CGCTCCTCG ATCATCGC 36

( 2 ) INFORMATION FOR SEQ ID NO: 15 :

( i ) SEQUENCE CHARACTERISTICS:
  ( A ) LENGTH: 37
  ( B ) TYPE: nucleic acid
  ( C ) STRANDEDNESS: single
  ( D ) TOPOLOGY: linear ( i i ) SEQUENCE DESCRIPTION:SEQ ID NO: 15 :

CGAATCAAAT CAAACTAACC CCTTTTCTC TCCTTTC 37

( 2 ) INFORMATION FOR SEQ ID NO: 16 :

( i ) SEQUENCE CHARACTERISTICS:
  ( A ) LENGTH: 18
  ( B ) TYPE: nucleic acid
  ( C ) STRANDEDNESS: single
  ( D ) TOPOLOGY: linear ( i i ) SEQUENCE DESCRIPTION:SEQ ID NO: 16 :

TCTAACTCTG TCATCATC 18

( 2 ) INFORMATION FOR SEQ ID NO: 17 :

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i i ) SEQUENCE DESCRIPTION:SEQ ID NO: 17 :

TTCTTCTTCT TCTTTCTTCT T 21

( 2 ) INFORMATION FOR SEQ ID NO: 18 :

( i ) SEQUENCE CHARACTERISTICS:
  ( A ) LENGTH: 23
  ( B ) TYPE: nucleic acid
  ( C ) STRANDEDNESS: single
  ( D ) TOPOLOGY: linear ( i i ) SEQUENCE DESCRIPTION:SEQ ID NO: 18 :

TAGGAAAGGC ACCCCCACAT TGG 60

( 2 ) INFORMATION FOR SEQ ID NO: 19 :

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i i ) SEQUENCE DESCRIPTION:SEQ ID NO: 19 :

CCCCTAAGAT CTCCTCCATG G 21

( 2 ) INFORMATION FOR SEQ ID NO: 20 :

( i ) SEQUENCE CHARACTERISTICS:
  ( A ) LENGTH: 41

(B) TYPE: nucleic acid
            (C) STRANDEDNESS: single
            (D) TOPOLOGY: linear (ii) SEQUENCE DESCRIPTION:SEQ ID NO: 20 :

CCCCTTTTTC TCTCCTTTCT CATTAGGACT TCCGCATCCG G                41

(2) INFORMATION FOR SEQ ID NO: 21 :

(i) SEQUENCE CHARACTERISTICS:
            (A) LENGTH: 41
            (B) TYPE: nucleic acid
            (C) STRANDEDNESS: single
            (D) TOPOLOGY: linear (ii) SEQUENCE DESCRIPTION:SEQ ID NO: 21 :

CCTCTCTTCT CTCTTCTCTC GCAAGTGTAC TCTCGATATG G                41

(2) INFORMATION FOR SEQ ID NO: 22 :

(i) SEQUENCE CHARACTERISTICS:
            (A) LENGTH: 25
            (B) TYPE: nucleic acid
            (C) STRANDEDNESS: single
            (D) TOPOLOGY: linear (ii) SEQUENCE DESCRIPTION:SEQ ID NO: 22 :

GCACTTTAAA TTTTCCCATT AGTCC                                  25

(2) INFORMATION FOR SEQ ID NO: 23 :

(i) SEQUENCE CHARACTERISTICS:
            (A) LENGTH: 20
            (B) TYPE: nucleic acid
            (C) STRANDEDNESS: single
            (D) TOPOLOGY: linear (ii) SEQUENCE DESCRIPTION:SEQ ID NO: 23 :

CCTGCGGGAT GTGGTATTCC                                        20

(2) INFORMATION FOR SEQ ID NO: 24 :

(i) SEQUENCE CHARACTERISTICS:
            (A) LENGTH: 40
            (B) TYPE: nucleic acid
            (C) STRANDEDNESS: single
            (D) TOPOLOGY: linear (ii) SEQUENCE DESCRIPTION:SEQ ID NO: 24 :

CCCCTTTTTC TCTCCTTTCT CAAGCCAGGA ATGGATGGCC                  40

(2) INFORMATION FOR SEQ ID NO: 25 :

(i) SEQUENCE CHARACTERISTICS:
            (A) LENGTH: 39
            (B) TYPE: nucleic acid
            (C) STRANDEDNESS: single
            (D) TOPOLOGY: linear (ii) SEQUENCE DESCRIPTION:SEQ ID NO: 25 :

CCTCTCTTCT CTCTTCTCTC CAGAAGTCTT GAGTTCTCC                   39

(2) INFORMATION FOR SEQ ID NO: 26 :

(i) SEQUENCE CHARACTERISTICS:
            (A) LENGTH: 16
            (B) TYPE: nucleic acid
            (C) STRANDEDNESS: single ( D ) TOPOLOGY: linear ( i i ) SEQUENCE DESCRIPTION:SEQ ID NO: 26 :

AGGGGGAAAG AAAAAA                                                                                    16

( 2 ) INFORMATION FOR SEQ ID NO: 27 :

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) SEQUENCE DESCRIPTION:SEQ ID NO: 27 :

AAATGGAAAA GGAAGGGAAA A                                                                              21

( 2 ) INFORMATION FOR SEQ ID NO: 28 :

( i ) SEQUENCE CHARACTERISTICS:
                ( A ) LENGTH: 15
                ( B ) TYPE: nucleic acid
                ( C ) STRANDEDNESS: single
                ( D ) TOPOLOGY: linear ( i i ) SEQUENCE DESCRIPTION:SEQ ID NO: 28 :

AAGGGAAAAA GGAAA                                                                                     15

( 2 ) INFORMATION FOR SEQ ID NO: 29 :

( i ) SEQUENCE CHARACTERISTICS:
                ( A ) LENGTH: 33
                ( B ) TYPE: nucleic acid
                ( C ) STRANDEDNESS: single
                ( D ) TOPOLOGY: linear ( i i ) SEQUENCE DESCRIPTION:SEQ ID NO: 29 :

AAAAGGGAGA CCCCAGAGGA AAGGGAAGAA AGA                                                                 33

( 2 ) INFORMATION FOR SEQ ID NO: 30 :

( i ) SEQUENCE CHARACTERISTICS:
                ( A ) LENGTH: 24
                ( B ) TYPE: nucleic acid
                ( C ) STRANDEDNESS: single
                ( D ) TOPOLOGY: linear ( i i ) SEQUENCE DESCRIPTION:SEQ ID NO: 30 :

AGAGGAGGAG GATGAAATAG ATGG                                                                           24

( 2 ) INFORMATION FOR SEQ ID NO: 31 :

( i ) SEQUENCE CHARACTERISTICS:
                ( A ) LENGTH: 11
                ( B ) TYPE: nucleic acid
                ( C ) STRANDEDNESS: single
                ( D ) TOPOLOGY: linear ( i i ) SEQUENCE DESCRIPTION:SEQ ID NO: 31 :

GGGGAAGAGG G                                                                                         11

( 2 ) INFORMATION FOR SEQ ID NO: 32 :

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) SEQUENCE DESCRIPTION:SEQ ID NO: 32 :

AAAAATAGAT GAAGGGGGAG A                                                          21

( 2 ) INFORMATION FOR SEQ ID NO: 33 :

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION:SEQ ID NO: 33 :

GAGGAAGAGG AAGA                                                                  14

( 2 ) INFORMATION FOR SEQ ID NO: 34 :

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION:SEQ ID NO: 34 :

TCCCCTTCTT CTTCTGCCGT TCC                                                        23

( 2 ) INFORMATION FOR SEQ ID NO: 35 :

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION:SEQ ID NO: 35 :

CTCCCTCCTT TCCTC                                                                 15

( 2 ) INFORMATION FOR SEQ ID NO: 36 :

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION:SEQ ID NO: 36 :

TCCCCCTTTC TTTTTT                                                                16

( 2 ) INFORMATION FOR SEQ ID NO: 37 :

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION:SEQ ID NO: 37 :

TCCCCCTTTC TTTTTT                                                                16

( 2 ) INFORMATION FOR SEQ ID NO: 38 :

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION:SEQ ID NO: 38 :

TTTACCTTTT CCTTCCCTTT T 21

( 2 ) INFORMATION FOR SEQ ID NO: 39 :

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION:SEQ ID NO: 39 :

TTCCCTTTTT CCTTT 15

( 2 ) INFORMATION FOR SEQ ID NO: 40 :

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION:SEQ ID NO: 40 :

TTTTCCCTCT GGGGTCTCCT TTCCTTCTT TCT 33

( 2 ) INFORMATION FOR SEQ ID NO: 41 :

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION:SEQ ID NO: 41 :

TTCTTCTTCT TCTTTCTTCT T 21

( 2 ) INFORMATION FOR SEQ ID NO: 42 :

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) SEQUENCE DESCRIPTION:SEQ ID NO: 42 :

TTTTCCTTTT CTGTTTCTTC TTCTTTCTTT CTTCTTT 37

( 2 ) INFORMATION FOR SEQ ID NO: 43 :

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i i ) SEQUENCE DESCRIPTION:SEQ ID NO: 43 :

CCCCTTCTCC C 11

( 2 ) INFORMATION FOR SEQ ID NO: 44 :

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION:SEQ ID NO: 44 :

TCTCCTCCTC CTACTTTATC TACC 24

-continued ( 2 ) INFORMATION FOR SEQ ID NO: 45 :

( i ) SEQUENCE CHARACTERISTICS:
( A ) LENGTH: 21
( B ) TYPE: nucleic acid
( C ) STRANDEDNESS: single
( D ) TOPOLOGY: linear ( i i ) SEQUENCE DESCRIPTION:SEQ ID NO: 45 :

TTTTTATCTA CTTCCCCCTC T 21

( 2 ) INFORMATION FOR SEQ ID NO: 46 :

( i ) SEQUENCE CHARACTERISTICS:
( A ) LENGTH: 14
( B ) TYPE: nucleic acid
( C ) STRANDEDNESS: single
( D ) TOPOLOGY: linear ( i i ) SEQUENCE DESCRIPTION:SEQ ID NO: 46 :

CTCCTTCTCC TTCT 14

( 2 ) INFORMATION FOR SEQ ID NO: 47 :

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION:SEQ ID NO: 47 :

AGGGGAAGAA GAAGACGGCA AGG 23

( 2 ) INFORMATION FOR SEQ ID NO: 48 :

( i ) SEQUENCE CHARACTERISTICS:
( A ) LENGTH: 15
( B ) TYPE: nucleic acid
( C ) STRANDEDNESS: single
( D ) TOPOLOGY: linear ( i i ) SEQUENCE DESCRIPTION:SEQ ID NO: 48 :

GAGGGAGGAA AGGAG 15

( 2 ) INFORMATION FOR SEQ ID NO: 49 :

( i ) SEQUENCE CHARACTERISTICS:
( A ) LENGTH: 37
( B ) TYPE: nucleic acid
( C ) STRANDEDNESS: single
( D ) TOPOLOGY: linear ( i i ) SEQUENCE DESCRIPTION:SEQ ID NO: 49 :

AAAAGGAAAA GACAAAGAAG AAGAAAGAAA GAAGAAA 37

NUCLEIC ACID SEQUENCE DETECTION BY TRIPLE HELIX FORMATION AT PRIMER SITE IN AMPLIFICATION REACTIONS

This is a continuation of application Ser. No. 08/000,922, filed Jan. 6, 1993, now abandoned which is a continuation of application Ser. No. 07/629,601, filed Dec. 17, 1990, now abandoned.

BACKGROUND OF THE INVENTION

The invention relates to the detection of DNA sequences, particularly following amplification by the polymerase chain reaction (PCR) or other methods of selective enzymatic amplification of a target sequence.

The polymerase chain reaction (PCR) is a rapid procedure for the in vitro enzymatic amplification of a specific segment of DNA. This method has proven extremely useful in detection of infectious agents in experimental and clinical settings. PCR-amplified products may be detected by a number of methods.

Syvanen et al. (Nuc. Acid. Res. 16: 11327, 1988) describe the use of oligonucleotides, labelled with biotin at their 5' ends, as primers in a PCR reaction. The resultant amplified DNA is denatured and hybridized to a radiolabelled probe; the desired product is then captured on an avidin matrix, through an avidin-biotin interaction, and detected by the presence of the radiolabelled probe.

Kemp et al. (Proc. Natl. Acad. Sci. USA 86: 2423, 1989) describe a method for colorimetric detection of specific DNA segments amplified by PCR. One set of oligonucleotide PCR primers is covalently attached to a label (for example, biotin or a site for binding a double-stranded DNA binding protein). The amplified double-stranded DNA product can be immobilized or bound by use of a reagent which has affinity for the label (e.g., a DNA binding protein to bind the site for the DNA binding protein) and the bound DNA detected (e.g., by labelling the biotinylated DNA with avidin linked to a detectable agent, such as horseradish peroxidase). The presence of the detectable agent (e.g., horseradish peroxidase) on the solid phase is then assayed using a chromogenic substrate by standard techniques.

Keller et al. (Anal. Biochem. 177:27, 1989) describe a microtiter plate sandwich hybridization assay for detection of PCR products. A well in a microtiter plate is covalently coupled to a capture DNA. PCR-amplified target DNA is denatured, hybridized to the capture DNA, and detected with a biotin-labelled detection probe.

Kenten et al. (publication of IGEN, Inc., Rockville, Md.) describe use of a biotin-labelled oligonucleotide primer and an ORIGEN®-labelled oligonucleotide primer. Following PCR, the biotin-labelled product is caused to bind to streptavidin and the presence of ORIGEN® assayed by electrochemiluminescent techniques.

Kumar et al. (Aids Research and Human Retroviruses 5:345, 1989) describe a probe shift assay. In this assay, PCR-amplified target DNA is denatured, hybridized to a complementary radiolabelled probe, and subjected to nondenaturing polyacrylamide gel electrophoresis before and after treatment with S1 nuclease. Increased migration of the DNA band following S1 nuclease treatment indicates the presence of target DNA.

SUMMARY OF THE INVENTION

In general, the invention features a method for detecting a nucleic acid. The method involves the steps of amplifying the nucleic acid in vitro using cycles of denaturation and amplification to yield product duplexes, and detecting product duplexes by hybridizing a third strand of nucleic acid to the product duplexes without denaturation. In preferred embodiments, the amplifying may be accomplished by polymerase chain reaction or ligase chain reaction (LCR). When used with PCR amplification, the method may include amplification by use of at least two PCR primers, one of the primers including a priming sequence hybridizable with the nucleic acid to be detected and one strand of a triple helix-forming sequence which need not hybridize to the original target DNA molecules, the other primer being hybridizable to the complement of the nucleic acid. When used with LCR, the method may include amplification by use of two or more pairs of ligatable LCR hybridization probes; such a pair may consist of one probe which includes a sequence hybridizable to the original target molecule and a second probe which includes an adjacent sequence that hybridizes to the target molecule and a triple helix-forming sequence that need not hybridize to the original target sequence but that is part of the ligated duplex molecules generated in LCR. The invention also features such PCR primers and LCR hybridization probes.

The invention further features a method for detecting the presence, in a biological sample, of a pathogen which includes an endogenous triple helix-forming nucleic acid sequence, involving hybridizing a third strand of nucleic acid to a duplex including the endogenous triple helix-forming sequence without denaturation of the duplex. The method will work on biological samples generally prepared in accordance with known hybridization procedures.

Preferred embodiments of both methods include the following features. The third strand of nucleic acid includes a polypyrimidine sequence of at least 15 nucleotides and may further include one or more purine residues, wherein each of the purine residues is flanked by 9 or more pyrimidine residues; alternatively, the third strand of nucleic acid includes a polypurine sequence of at least 15 nucleotides and may further include one or more pyrimidine residues, wherein each of the pyrimidine residues is flanked by 9 or more purine residues. The third strand may include one or more modified residues. The third strand of nucleic acid may be covalently attached to a solid support, preferably, a microparticle. The target sequence nucleic acid is detected using an FCA (fluorescence concentration assay); format, a PCFIA (particle concentrated fluorescence immunoassay) format, or a microtiter well format. The third strand of nucleic acid may be covalently attached to a reporter group, preferably, sulforhodamine or alkaline phosphatase. The nucleic acid may be detected by enhanced ethidium bromide fluorescence following contact with a third strand. The duplex PCR product is isolated prior to detection. More than one nucleic acid duplex can be detected without separating the target duplexes, and detection of additional nucleic acid duplexes involves hybridizing each of the additional duplexes with a third strand of nucleic acid. The third strand may consist of a single molecule that accomplishes specific duplex capture as well as detection. Alternatively, those two functions may be on two or more separate single-stranded molecules which hybridize to different locations on the duplex being detected and, together, make up the "third strand" as we use that term.

In other preferred embodiments, the nucleic acid is derived from *M. paratuberculosis*; the nucleic acid is derived from a retrovirus; the retrovirus is a caprine arthritis encephalitis virus; the retrovirus is a human immunodeficiency virus, and the third strand includes at least 15 consecutive nucleotides of the sequence: tcccccttctttttt (SEQ ID No.: 37) or at least 15 consecutive nucleotides of the sequence: tttaccttttccttcccttt (SEQ ID NO.: 38); the retrovirus is a feline leukemia virus, and the third strand includes the sequence: ttccctttttccttt (SEQ ID NO.: 39) or includes at least 15 consecutive nucleotides of the sequence: ttttccctctggggtctccttcccttctttct (SEQ ID NO.: 40); the retrovirus is a feline immunodeficiency virus, and the third strand includes at least 15 consecutive nucleotides of the sequence: ttcttcttctttcttctt (SEQ ID NO.: 41) or at least 15 consecutive nucleotides of the sequence: ttttccttttctgtttcttct-tctttcttttcttctt (SEQ ID NO.: 42); the nucleic acid is derived from a human papilloma virus; the human papilloma virus is HP-16, and the third strand includes the sequence: cccct-tctccc (SEQ ID NO.: 43) or at least 15 consecutive nucle-otides of the sequence: tctcctcctcctactttatctacc (SEQ ID NO.: 44); the human papilloma virus is HP-18, and the third strand includes at least 15 consecutive nucleotides of the sequence: ttttatctacttccccctct (SEQ ID NO.: 45) or includes the sequence: ctccttctccttct (SEQ ID NO.: 46); and the nucleic acid is derived from a hepatitis B virus, and the third strand includes at least 15 consecutive nucleotides of the sequence: aggggaagaagaagacggcaagg (SEQ ID NO.: 47) or includes the sequence: gagggaggaaaggag (SEQ ID NO.: 48).

The invention yet further features a purified single-stranded nucleic acid probe including at least 15 consecutive nucleotides of the triple helix-forming sequence: ctctttc-ctctcttttcccc (SEQ ID NO.: 9) or ctctcttctctcttctctcc (SEQ ID NO.: 10).

An alternative method for detecting a nucleic acid is also featured. The method involves a competitive triple helix binding assay which includes the steps of amplifying the nucleic acid in vitro using cycles of denaturation and ampli-fication to yield product duplexes, hybridizing a third strand of nucleic acid to the product duplexes without denaturation, hybridizing any free third strand with a nucleic acid hook sequence covalently bound to a solid support, and measuring the amount of product duplex as the inverse measure of the quantity of the third strand bound to the hook sequence. In preferred embodiments, the nucleic acid hook sequence is double-stranded.

The methods of the invention are incorporated into a kit for detecting a nucleic acid. The kit includes a single-stranded nucleic acid probe capable of specifically hybrid-izing to a triple helix-forming sequence of the nucleic acid, the probe being covalently attached to a reporter group, and a reagent for detecting the reporter group bound to the nucleic acid.

In preferred embodiments, the single-stranded nucleic acid is covalently attached to a solid support; the kit includes a second single-stranded nucleic acid capable of specifically hybridizing to a triple helix-forming sequence of the nucleic acid, and the second single-stranded nucleic acid is covalently attached to a solid support; the solid support is a microparticle; the nucleic acid is detected using a microtiter well format, an FCA format, or a PCFIA format; and the reporter group is alkaline phosphatase or sulforhodamine. To facilitate amplification, the kit may further feature at least two PCR primers, one of the primers including a priming sequence hybridizable with the nucleic acid to be detected and one strand of a triple helix-forming sequence which need not hybridize to the original target DNA molecule, the other primer being hybridizable to the complement of the nucleic acid. Alternatively, the kit may include two or more pairs of ligatable LCR hybridization probes; such a pair may consist of one probe which includes a sequence hybridizable to the original target molecule and a second probe which includes an adjacent sequence that hybridizes to the target molecule and a triple helix-forming sequence that need not hybridize to the original target sequence but that is part of the ligated duplex molecules generated in LCR.

By "triple helix-forming" is meant (a double-stranded nucleotide sequence) capable of specifically binding, e.g., by Hoogsteen hydrogen bonds (Hoogsteen, *Acta. Cryst.* 12:822, 1959), to a third strand of nucleic acid. Triple helix-forming sequences include, without limitation, stretches of polypurine and polypyrimidine residues. By "endogenous triple helix-forming sequence" is meant a sequence which occurs naturally in the target sequence (e.g., is not introduced by use of PCR or LCR) and is capable of forming a triple helix. By "target sequence" is meant a nucleic acid sequence, the presence or absence of which is desired to be detected. In the context of a preferred appli-cation of the methods of the invention, it is a sequence derived from a pathogenic organism. "Modified nucle-otides" include, but are not limited to, protonated or methy-lated nucleotides, preferably, cytosine residues. By "reporter group" is meant any molecule which facilitates such target sequence detection, including, without limitation, sulfor-hodamine and alkaline phosphatase. By "microparticle" is meant any small solid support, including, without limitation, a Latex microparticle. By "amplification" is meant an increase in number of a particular nucleic acid sequence and may be accomplished, without limitation, by the in vitro methods of polymerase chain reaction or ligase chain reac-tion. By "duplex" is meant a double-stranded nucleic acid sequence. By "priming sequence" is meant a single-stranded nucleic acid which hybridizes to a single-stranded target sequence template and facilitates PCR amplification. Such a priming sequence would be included in a "PCR primer". By "LCR hybridization probe" is meant one of a pair of ligatable single-stranded nucleic acid sequences which hybridizes to a single-stranded target sequence and facili-tates ligase chain reaction. As used herein, the term includes a probe containing a region complementary to, and therefore capable of hybridizing to, the original target sequence (i.e., the "target-hybridizing sequence") as well as a probe which includes both a region complementary to the target sequence and a triple helix-forming sequence that need not hybridize to the original target sequence but that is part of the ligated duplex molecules generated in LCR. By "adjacent" is meant (two probes) positioned closely enough on a DNA template to be joined following a standard DNA ligation reaction. By "purified nucleic acid" is meant nucleic acid separated from other sequences with which it is naturally associated. By "probe" is meant a third strand of DNA which specifically binds, by triple helical interactions, to its complementary target sequence. By a "hook sequence" is meant a single-stranded or double-stranded oligonucleotide which hybrid-izes to a particular nucleic acid and facilitates its detection. The hook sequence may be covalently bound to a solid support to allow nucleic acid capture prior to detection.

The methods of the invention facilitate the rapid, specific, and automated isolation and/or detection of a nucleic acid target sequence. These methods have a number of advan-tages. For example, because stable triple helical complexes form at room temperature, there is no need for chemical or thermal denaturation of the double-stranded target sequence product prior to detection. In addition, isolation and/or detection of a target sequence is accomplished using triplex probes bound to capture molecules or reporter groups. Many such methods of capture and many such reporter groups exist, allowing the methods of the invention to be adapted to several formats, some of which are described below. Further, triplex probes hybridize efficiently only with the double-stranded target sequence. As a result, single-stranded PCR primers do not compete to any appreciable extent with target sequence for interaction with the triplex probes, and very little capture and/or detection reagent (i.e., triplex probe) is required. Finally, many different PCR products can be separately captured or detected since, in principle, any triple helix-forming sequence (for example, any polypyrimidine sequence of the appropriate length) can be used to introduce, during PCR amplification, a triple helix binding site into the target sequence. Each of these binding sites can then be separately isolated and/or detected using the methods of the invention.

DESCRIPTION OF THE PREFERRED EMBODIMENTS

The drawings will first briefly be described.

Drawings FIG. 1 is a schematic representation of the PCR-directed incorporation of a triple helix-forming sequence into a target sequence and its triple helical detection.

FIG. 8 is a list of genes whose sequences include a homopolymer tract of 25 base pairs or greater.

METHODS

Figure 1:
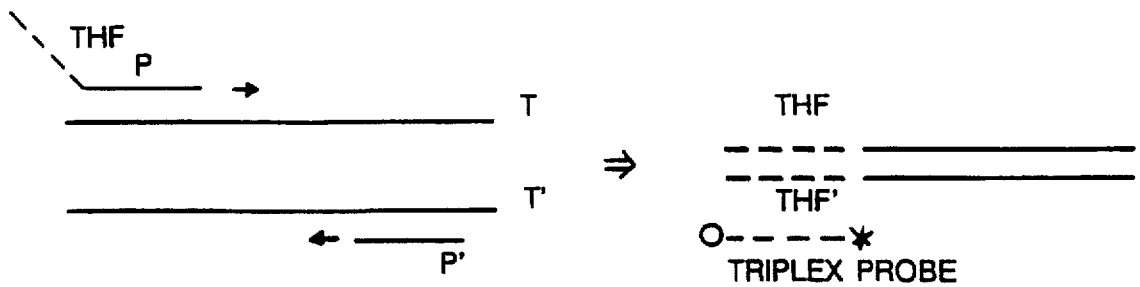

The methods of the invention allow detection of any target sequence containing a triple helix-forming region. Such a triple helix-forming region may be naturally-occurring (i.e., endogenous) or it may be incorporated into the target sequence during amplification in vitro, e.g., by polymerase chain reaction (PCR) or ligase chain reaction (LCR). PCR primers used for such an amplification reaction, termed "triplex primers" or "triple helix-forming primer", contain (1) a sequence complementary (and therefore capable of hybridizing) to single-stranded target sequence (P and P') and (2) a sequence which, when incorporated into the amplified nucleic acid, is capable of forming a triple helix (THF and THF'; FIG. 1). The basic PCR reaction is well known, and there is no need to provide a detailed description of it here (see, e.g., U.S. Pat. No. 4,683,202, hereby incorporated by reference). Following amplification, the target sequence present in the resulting products is detected using a "triplex probe" (i.e., a single-stranded probe having a sequence which binds to amplified products having a duplex triple helix-forming target sequence and allows isolation of the target sequence) (FIG. 1). The triplex probes may be bound to a solid phase which facilitates capture (O, FIG. 1). In one example, this solid phase is a Latex microparticle which may be isolated by centrifugation or by capture on a fluorescence concentration analyzer (FCA) plate following vacuum filtration (see below). In addition, the triplex probe may include a "detection sequence" (i.e., a sequence which binds to a duplex target sequence and allows the target sequence to be assayed). The detection sequence is generally bound to a reporter group (*, FIG. 1), which indicates the presence of the duplex target sequence. In one example, this reporter group is sulforhodamine, a substrate which is detected by fluorescence assay. A single triplex probe can be bound both to a solid phase and to a reporter group. Alternatively, two triplex probes can be used, one bound to a solid phase and a second bound to a reporter group. In the latter case the solid phase-bound probe and the reporter-bound probe bind at different triple helix-forming sites on the duplexes to be detected.

Figure 2:
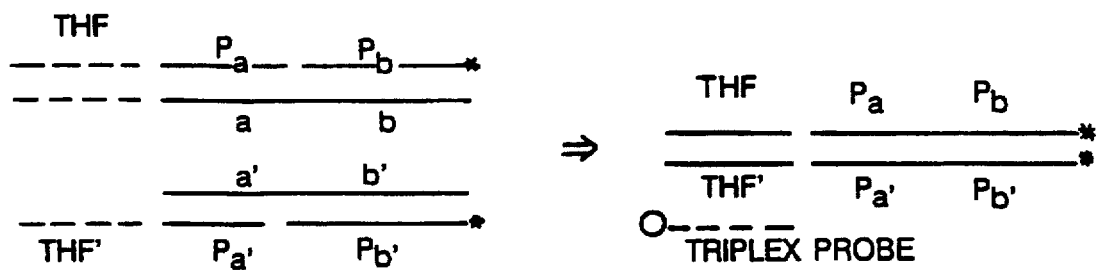
FIG. 2 is a schematic representation of the LCR-directed incorporation of a triple helix-forming sequence into a target sequence and its triple helical detection.

The LCR reaction is similarly well known (see, e.g., European Patent Application No. 0 336 731 A2, hereby incorporated by reference). LCR incorporation of a triple helix-forming region is accomplished in two steps. First, target sequence DNA is denatured and to the appropriate single strand is annealed a pair of LCR hybridization probes (e.g., LCR probe 1 and LCR probe 2) which are complementary to adjacent sequences (a and b, FIG. 2). In one example, LCR probe 1 includes a "target-hybridizing sequence" ($P_a$, FIG. 2) and one strand of a triple helix-forming sequence (THF, FIG. 2). LCR probe 2 includes an adjacent target-hybridizing sequence ($P_b$, FIG. 2) and a detectable label (e.g., sulforhodamine; *; FIG. 2). In the same annealing reaction, another pair of adjacent probes is hybridized to the opposite strand of target DNA. In this case, LCR probe 1' includes a target-hybridizing sequence ($P_a'$, FIG. 2) and one strand of the triple helix-forming sequence (THF', FIG. 2); and LCR probe 2' includes a target-hybridizing sequence ($P_b'$, FIG. 2), and it may be bound to the same detectable label (*; FIG. 2). LCR probes 1 and 2 and LCR probes 1' and 2' are ligated together, and the duplexes are denatured and re-annealed, allowing complex formation between the the newly-ligated probe strands. Capture is accomplished with a third strand of nucleic acid (i.e., a "triplex probe", FIG. 2) which forms a triple helix with the double-stranded triple helix-forming sequence. The third strand may, e.g., be attached to a solid support (O, FIG. 2), such as a microparticle, to aid in product duplex isolation (e.g., as described herein). Triple helices are assayed, e.g., by measuring sulforhodamine fluorescence.

In general, the duplex-binding sequences of the triplex probes used in these studies are stretches of polypyrimidine or polypurine residues of identical polarity and complementary to the polypurine or polypyrimidine tract (respectively) of the target sequence to be detected. These polypurine or polypyrimidine sequences are, preferably, 15 nucleotides or greater in length, optimally, 20 nucleotides. Such probe sequences cannot form a stable Watson-Crick complex or parallel helical complex (i.e., Hoogsteen complex) with the single-stranded primers but can stably interact only with a duplex primer sequence bound to its Watson-Crick partner (i.e., incorporated into the sequence of the double-stranded target sequence). For example:

| | |
|---|---|
| → 5' ggaaggaaagaaggag | 3' Target sequence (SEQ ID NO.: 1) |
| ← 3' CCTTCCTTTCTTCCTC | 5' Triplex Primer (SEQ ID NO.: 2) |
| 5' CCTTCCTTTCTTCCTC | 3' Triple Helical Probe (SEQ ID NO.: 3) |

This observation underlies the utility of the invention; a third strand probe does not efficiently interact with a single-stranded primer sequence until such a sequence is incorporated into a double-stranded PCR product.

Reaction conditions for triple helix formation have been determined and are described herein and in, for example, Griffin and Dervan (*Science* 245:967, 1989); Moser and Dervan (*Science* 238:645, 1987); Lyamichev et al. (*Nucl. Acids Res.* 16:2165, 1988); Strobel et al. (*J. Am. Chem. Soc.* 110: 7927, 1988); Povsic and Dervan (*J. Am. Chem. Soc.* 111:3059, 1989); and Maher et al. (*Science* 245:725, 1989).

Triple helix-forming sequences are not limited to polypyrimidine or polypurine stretches. Certain purine-pyrimidine-purine tracts also form stable triple helices and provide additional sequence versatility for this approach. For example, an adenosine residue interrupting a polypyrimidine target sequence can be accommodated with a guanosine residue in the triplex probe strand (Griffin and Dervan, *Science* 245:967, 1989). Base pair mismatches may be compensated for by adjustment of solution conditions, for example, by maintaining a pH of between 6.2 and 7.0, and/or by inclusion of 10% ethanol, and/or by adjustment of the reaction temperature to 23° C. or below (for example, 0° C.) (see, for example, Griffin and Dervan, *Science* 245:967, 1989). Triple helical interactions are also improved by binding an intercalating drug such as acridine to the end of the single-stranded triplex probe strand (i.e., the third strand of nucleic acid). Upon binding to a duplex target sequence, the triplex probe-bound drug intercalates into the duplex DNA and contributes to the total binding constant. There are reports that the use of a third strand of nucleic acid bound to an intercalating drug allows specific triple helical interactions using third strands of DNA which are of a shorter length, e.g., 8 to 10 nucleotides of polypyrimidine. In addition, triple helix-forming sequences or triplex probe sequences may include one or more modified nucleotide bases, for example, protonated, methylated, or halogenated bases, e.g., cytosines.

Analysis of any number of DNA target sequences in a single PCR reaction mixture, or amplificate, may be accomplished using the methods of the invention. By incorporating different capture sequences into the PCR primers, a single PCR reaction may be run and target sequences may be isolated separately and detected using one or more reporter group-labelled detection sequences. Alternatively, by incorporating a common capture sequence into the PCR primers, many target sequences may be isolated simultaneously and then individually assayed using unique detection sequences, each bound to a different reporter group. Such reporter groups would be differentiated, for example, by measuring unique fluorescence properties (i.e., each reporter group is detected at a different wavelength).

The methods of the invention allow detection of any target sequence (i.e., from any organism) whose sequence, or a portion thereof, has been determined. PCR primers and triplex probes would be designed as described herein and amplification and detection of the sequence, similarly, carried out by the methods herein. The methods of the invention are particularly well-suited to the detection of retroviruses, for example, lentiviruses. Inspection of many retroviral sequences reveals the presence of unique triple helix-forming sequences, often in the viral LTR. For example, the following viral genomes include one or more triple helix-forming sequences: feline immunodeficiency virus, feline leukemia virus; human immunodeficiency virus, type 1; hepatitis B virus; and human papilloma viruses, HP-16 and HP-18.

A very small quantity of target sequence (e.g., nucleic acid isolated from a pathogenic organism) is required for detection by these methods. The nucleic acid to be amplified and/or detected may be isolated from tissue, blood, fecal samples or the like by techniques well known to those skilled in the art.

A kit which facilitates triple helical detection of target sequences may encompass any or all of the embodiments described herein.

Experimental Information

The present invention will be further illustrated by the following examples. In the first set of examples, a triple helix-forming sequence is introduced by PCR into *M. paratuberculosis*-derived nucleic acid. The sequence is then detected using either a microtiter well or a fluorescence concentration assay (FCA) plate format and the reporter groups, alkaline phosphatase or sulforhodamine (Texas Red). In a separate set of examples, an endogenous triple-helix forming sequence is exploited for detection of feline immunodeficiency virus (FIV). Finally, to illustrate the general utility of the method, exogenous triple helix-forming sequences (incorporated by PCR) are exploited for detection of caprine encephalitis arthritis virus (CEAV) and human immunodeficiency virus, type 1 (HIV-1), using an FCA plate format and a sulforhodamine reporter group. These examples are not limiting to the invention.

Triple helical detection of PCR-amplified nucleic acid target sequences

PCR primers specific for the *M. paratuberculosis* (*M.pt.* or *M.pt.*)-derived sequence IS900 were prepared; the primer sequences were based on the published *M.pt.* sequence described in Green et al. (*Nucl. Acids Res.* 17:9063, 1989) and were of the following sequence (5'→3'). (The first nucleotide of the *M. Pt.*-specific sequence is underlined):

| | |
|---|---|
| cccctttttctctcctttctcggacaatgacggttacgg | Triplex IS210A (SEQ ID NO.: 4) |
| cctctcttctctctttctcggacaatgacggttacgg | Triplex IS210B (SEQ ID NO.: 5) |
| cccctttttctctcctttctccaaggcgatcagcaacgcgg | Triplex IS435A (SEQ ID NO.: 6) |
| cggacaatgacggttacgg | M.pt.X (SEQ ID NO.: 7) |
| caaggcgatcagcaacgcgg | M.pt.Y (SEQ ID NO.: 8) |
| ctctttcctctcttttttcccc-NH$_2$ | Triplex Probe A (SEQ ID NO.: 9) |
| ctctcttctctcttctctcc-NH$_2$ | Triplex Probe B (SEQ ID NO.: 10) |

The triplex primers contain two domains: (1) a sequence at the 3' end specific for PCR priming of the complementary sequences in the *M.pt.* genomic DNA and (2) a polypyrimidine sequence at the 5' end which provides a triple helix-forming sequence. Triplex probe A (SEQ ID NO.: 9) is bound to a solid support and constitutes a capture sequence; triplex probe B (SEQ ID NO.: 10) is bound to a reporter group and constitutes a detection sequence. In other cases, the target sequence-specific region and the triple helix-forming sequence may overlap in part or in full (for example, in the case of lentiviral endogenous polypurine sequences, see below).

Oligonucleotide primers were synthesized using standard phosphoramidite chemistry on an Applied Biosystems 381-A DNA synthesizer. All nucleic acids were stripped from their controlled pore glass supports and deblocked using concentrated reagent ammonium hydroxide and an 8–16 hr. standard incubation time at 55° C. Oligonucleotides were desalted by gel exclusion chromatography and transferred to 0.01M MES buffer, pH 5.5 using Sephadex G10 column chromatography. Amino groups were added to the 3' termini of the primers using a 3' amino-on controlled pore glass support (Clontech, Inc.; Palo Alto, Calif.).

M.pt. genomic DNA was prepared as follows. M.pt. cells were disrupted by heating at 120° C. for 5 min. in 0.2N NaOH, and DNA was isolated from the cell debris by standard phenol/chloroform extraction. PCR amplification of M. pt. DNA was performed using one or two of the triple helix-forming primers, triplex IS210A (SEQ ID NO.: 4), triplex IS210B (SEQ ID NO.: 5), or triplex IS435A (SEQ ID NO.: 6), above. In addition, control PCR product was prepared using primers, M.pt.X (SEQ ID NO.: 7) and M.pt.Y (SEQ ID NO.: 8), which included IS900-derived sequences but lacked any triple helix-forming sequence. PCR reactions were conducted using the standard reaction conditions recommended by Cetus (Perkin-Elmer Cetus, Norwalk, Conn.) and included 0.7 μmol primer. Primer concentrations were estimated by determination of absorption at 260 nm. Individual primer millimolar extinction values were calculated using the high temperature molar extinction coefficient for homopolymer strands.

Probe sequences were bound to Latex microparticles (also referred to as Latex beads) as follows. Latex microparticles (i.e., 1.0μ carboxylate microspheres; Polysciences, Inc., Warrington, Pa.) bearing carboxyl groups were activated in situ by incubating for 2 hr. at pH 5.5 with a 5:1 molar ratio (with respect to carboxyl groups) of 1-ethyl-3-3 (dimethylaminopropyl)-carbodiimide) (EDAC; Sigma Chemical Co., St. Louis, Mo.). Probe sequences bearing a single primary amino group (incorporated during automated chemical synthesis) were mixed with the activated Latex microparticles and the reaction was allowed to proceed for 15 min. at 25° C. in 0.1M MES, pH 5.5. The reaction was terminated by the addition of excess 0.1M glutamic acid (i.e., 100 μl glutamic acid/ 1 ml reaction mixture). Microparticles were washed 4 times with excess 0.1M MES, pH 5.5 and one time with water. The beads were resuspended in water to a density of 2.5% (w/v) solids based on original amounts used.

Probe sequences may be bound to alkaline phosphatase (AP) by the method of Jablonski et al. (Nucl. Acids Res. 14:6115, 1986).

EXAMPLE 1

PCR-amplified M.pt.-derived sequence IS900 was detected using Probe A (SEQ ID NO.: 9)- or Probe B (SEQ ID NO.: 10)-labelled Latex microparticles and a polyacrylamide gel format as follows. M.pt. genomic DNA was amplified using either triplex IS435A (SEQ ID NO.: 6) and triplex IS210A (SEQ ID NO.: 4) to produce PCR A=A, or triplex IS435A (SEQ ID NO.: 6) and triplex IS210B (SEQ ID NO.: 5) to produce PCR A=B. Following PCR amplification, 5 μl of the amplificate was mixed with 10 μl of 0.5μ Latex microparticles and 4 μl 5×AP triple helix buffer (1.6% Tween 20; 10 mM spermine; 1.0M MES, pH5.5) and 1 μl H₂O. The reaction was carried out at room temperature for 30 min. Triple helix formation was assessed following electrophoretic separation of bound (i.e., triple helical) product from free product on a 4% non-denaturing polyacrylamide gel. PCR products were visualized with ethidium bromide.

Table 1 shows that triplex probes A (SEQ ID NO.: 9) and B (SEQ ID NO.: 10) specifically recognize and bind the appropriate products present in a PCR product mixture.

TABLE 1

| | | | | | | |
|---|---|---|---|---|---|---|
| Probe Aᵃ-microparticles | − | + | − | − | + | − |
| Probe Bᵇ-microparticles | + | − | − | + | − | − |
| PCR A = Aᶜ | + | + | + | − | − | − |
| PCR A = Bᵈ | − | − | − | + | + | + |
| Expected Binding | − | + | − | + | + | − |
| Observed Binding | − | + | − | + | + | − |

ᵃSEQ ID NO.: 9
ᵇSEQ ID NO.: 10
ᶜPCR amplificate prepared as described above using M.pt. genomic DNA and primer, triplex IS435A (SEQ ID NO.: 6) and triplex IS210A (SEQ ID NO.: 4).
ᵈPCR amplificate prepared as described above using M.pt. genomic DNA and primers, triplex IS435A (SEQ ID NO.: 6) and triplex IS210B (SEQ ID NO.: 5).

EXAMPLE 2

Triple helical interactions were also assessed by a sandwich assay using labelled carboxy-Latex microspheres (i.e., Latex microparticles) in a microtiter well format; triple helices were visualized using alkaline phosphatase-labelled triplex probes. M.pt. genomic DNA was amplified using either triplex primers IS435A (SEQ ID NO.: 6) and IS210B (SEQ ID NO.: 5) (to yield the triple helix-forming product, PCR A=B) or standard primers M.pt.X (SEQ ID NO.: 7) and M.pt.Y (SEQ ID NO.: 8) (to yield the product, M.pt. X=Y). 5 μl of PCR amplificate was mixed with 10 μl of 0.5μ Probe A (SEQ ID NO.: 9)-labelled Latex microparticles, 1 μl of varying amounts of Probe B (SEQ ID NO.: 10)-labelled alkaline phosphatase, 4 μl 5×AP triple helix buffer, and 5 μl H₂O. Triple helix formation was allowed to proceed for 30 minutes at room temperature. Following incubation, the reaction was centrifuged for 2 min. at 14,000 rpm in a microcentrifuge, and the supernatant was removed. Microparticles were then washed twice with 1×Enzyme Amplified Capture Buffer (EAC Buffer; 1M MES, pH 5.5, 0.02% w/v sodium azide, 1M NaCl, 0.01M Spermine, 1.5% w/v Tween 20), followed by microparticle isolation by centrifugation as above. Microparticles were then resuspended in 50 μl Diethanolamine Enzyme Assay Buffer (DEA Buffer; 0.1M diethanolamine, 5 mM MgCl₂, pH9.5) and transferred to 96-well microtiter plates (Dynatech Inc., Chantilly, Va.). Colorimetric enzyme assay reaction was initiated by the addition of 50 μl Alkaline Phosphatase Assay Buffer (AP Buffer; 0.1M diethanolamine, pH9.5, 5 mM MgCl₂, 6 mg/ml paranitrophenol phosphate) at room temperature. Alkaline phosphatase activity was assayed over a 20 min. interval in a Molecular Devices $V_{max}$ microtiter plate reader (Molecular Devices Inc., Menlo Park, Calif.). Table 2 shows that the PCR-amplified product, PCR A=B, which contains triple helix-forming sequences is detected using triplex probes A (SEQ ID NO.: 9) and B (SEQ ID NO.: 10). The control product, M.pt. X=Y, which does not contain a triple helix-forming sequence is not detected under these assay conditions.

TABLE 2

| | | | | | | |
|---|---|---|---|---|---|---|
| Probe B-Alkaline phosphataseᵃ (dilution) | 1/5 | 1/10 | 1/50 | 1/5 | 1/10 | 1/50 |
| PCR A = Bᵇ | 5 | 5 | 5 | | | |
| M.pt. X = Yᶜ | | | | 5 | 5 | 5 |

TABLE 2-continued

| Expected Color | + | + | + | − | − | − |
|---|---|---|---|---|---|---|
| Observed Color | + | + | +/− | +/− | − | − |

<sup>a</sup>Dilution of a 1 μg/ml Probe B (SEQ ID NO.: 10) sequence bound to alkaline phosphatase.
<sup>b</sup>PCR amplificate prepared as described above using M.pt. genomic DNA and primers, triplex IS435A (SEQ ID NO.: 6) and triplex IS210B (SEQ ID NO.: 5).
<sup>c</sup>PCR amplificate prepared as described above using M.pt. genomic DNA and primers, M.pt.X (SEQ ID NO.: 7) and M.pt.Y (SEQ ID NO.: 8).

To determine the specificity of the triple helical interactions, PCR amplificates described above were assayed using either Probe A (SEQ ID NO.: 9)- or oligo-dT-labelled microparticles. Binding was detected (as above) by measuring alkaline phosphatase activity. A (+) value was defined as visible color; a (−) value was defined as a white background.

Table 3 shows that Probe A (SEQ ID NO.: 9), but not oligo (dT), selectively detected PCR products amplified using primer triplex IS210A (SEQ ID NO.: 4) and/or triplex IS435A (SEQ ID NO.: 6).

TABLE 3

| Probe A<sup>a</sup>-microparticles | + | + | + | − | − | − |
|---|---|---|---|---|---|---|
| Oligo dT-microparticles | − | − | − | + | + | + |
| Probe B<sup>b</sup>-alkaline phosphatase | + | + | + | + | + | + |
| PCR A = B<sup>c</sup> | + | | | + | | |
| PCR A = A<sup>d</sup> | | + | | | + | |
| M.pt. X = Y<sup>e</sup> | | | + | | | + |
| Expected Color | + | − | − | − | − | − |
| Observed Color | ++ | + | +/− | +/− | +/− | − |

<sup>a</sup>SEQ ID NO.: 9
<sup>b</sup>SEQ ID NO.: 10
<sup>c</sup>PCR amplificate prepared as described above using M.pt. genomic DNA and primers, triplex IS435A (SEQ ID NO.: 6) and triplex IS210B (SEQ ID NO.: 5).
<sup>d</sup>PCR amplificate prepared as described above using M.pt. genomic DNA and primer, triplex IS210A (SEQ ID NO.: 4) and triplex IS435A (SEQ ID NO.: 6).
<sup>e</sup>PCR amplificate prepared as described above using M.pt. genomic DNA and primers, M.pt.X (SEQ ID NO.: 7) and M.pt.Y (SEQ ID NO.: 8).

PCR product capture and detection was dependent upon the quantity of Probe A (SEQ ID NO.: 9)-labelled beads added to the reaction mixture. This result is shown in Table 4. A 30 μl reaction contained 10 μl PCR amplificate, 1 μl of a 1:10 dilution of Probe B (SEQ ID NO.: 10)-labelled alkaline phosphatase (of concentration 0.1 μg/ml) and decreasing amounts (ranging from 0.25 to 0.10 μg/ml) of Probe A (SEQ ID NO.: 9)-labelled 1μ Latex microparticles in 17 μl of water and 6 μl of 5×AP triple helix buffer. Triple helix formation was allowed to proceed for 30 minutes at room temperature. Following incubation, the reaction was centrifuged for 1 minute at 14,000 rpm in a microcentrifuge, the supernatant was removed, and the microparticles were washed twice with 1×Enzyme Amplified Capture Buffer (as described above) followed by particle isolation by centrifugation (at 14,000 rpm for 2 min.). The microparticles were then resuspended in 50 μl Diethanolamine Enzyme Assay Buffer and transferred to microtiter wells (as described above). The colorimetric enzyme assay reaction was initiated by the addition of 50 μl Alkaline Phosphatase Assay Buffer. Alkaline phosphatase was assayed over a 20 minute interval in a Molecular Devices V$_{max}$ microtiter plate reader. Values shown in Table 4 were calculated from initial velocity measurements. The numbers represent mOD/min. Table 4 shows that the PCR product resulting from amplification using triplex primers IS435A (SEQ ID NO.: 6) and IS210B (SEQ ID NO.: 5) (i.e., PCR A=B) was detected with varying amounts of probe A (SEQ ID NO.: 9)-labelled Latex microparticles.

TABLE 4

| Volume of Probe A<sup>a</sup>-microparticles | 5 μl | 4 μl | 3 μl | 2 μl |
|---|---|---|---|---|
| PCR A = B<sup>b</sup> | 139.7 | 113.4 | 156.7 | 102.7 |
| M.pt. X = Y<sup>c</sup> | 22.3 | 4.4 | 5.3 | 4.0 |

<sup>a</sup>SEQ ID NO.: 9
<sup>b</sup>PCR amplificate prepared as described above using M.pt. genomic DNA and primers, triplex IS435A (SEQ ID NO.: 6) and triplex IS210B (SEQ ID NO.: 5).
<sup>c</sup>PCR amplificate prepared as described above using M.pt. genomic DNA and primers, M.pt.X (SEQ ID NO.: 7) and M.pt.Y (SEQ ID NO.: 8).

To assess the "worst case" contribution of background binding (i.e., by primer dimer accumulation in the absence of target sequence nucleic acid), M.pt. genomic DNA target sequence was PCR-amplified using primers, triplex IS435A (SEQ ID NO.: 6) and triplex IS210B (SEQ ID NO.: 5) (+). A negative amplificate (−) was prepared by performing PCR using the primers, triplex IS435A (SEQ ID NO.: 6) and triplex IS210B (SEQ ID NO.: 5) in the absence of any added target sequence. (+) and (−) PCR amplificates were mixed in varying proportions to a constant volume of 5 μL. Detection was performed in a 25 μl reaction mixture containing the mixed amplificates, 4 μl Probe A (SEQ ID NO.: 9)-labelled microparticles, 1 μl of a 1:10 dilution of Probe B (SEQ ID NO.: 10)-labelled alkaline phosphatase, and 5 μl of 5×AP triple helix buffer. Reaction mixtures were processed as described above, and alkaline phosphatase activity was measured in mOD/min.

TABLE 5

| + PCR A = B (μl) | 0 | 1 | 2 | 3 | 4 | 5 |
|---|---|---|---|---|---|---|
| − PCR A = B (μl) | 5 | 4 | 3 | 2 | 1 | 0 |
| Alkaline phosphatase activity | 32.0 | 43.7 | 34.5 | 43.1 | 79.2 | 85.1 |

Table 5 shows that in the "worst case" (i.e., at 5 μl PCR A=B: 5 μl negative control), the signal/background ratio was about 2.7:1.

EXAMPLE 3

Triple helical formation was also detected using a Fluorescence Concentration Analyzer (FCA) format. The assay was performed as described for Table 2. Following triple helix formation, the reaction mixture was transferred to an FCA plate (Pandex Corp., Mundelein, Ill.) held under vacuum. The microparticles were then washed once with 50 μl 2×AP triple helix buffer. 30 μl of DEA Buffer was added, and the plate was photographed following a 60 minute incubation. Results of this analysis are shown in Table 6. A (+) value was defined as visible color; a (−) value was defined as a white background.

TABLE 6

| Probe A<sup>a</sup>-microparticles | + | + | + | + | + | + |
|---|---|---|---|---|---|---|
| Probe B<sup>b</sup>-alkaline phosphatase | + | + | + | + | + | + |
| PCR A = B<sup>c</sup> | + | + | + | − | − | − |
| M.pt. X = Y<sup>d</sup> | − | − | − | + | + | + |

TABLE 6-continued

| Expected Color | + | + | + | − | − | − |
|---|---|---|---|---|---|---|
| Observed Color | + | + | + | − | − | − |

[a]SEQ ID NO.: 9
[b]SEQ ID NO.: 10
[c]PCR amplificate prepared as described above using M.pt. genomic DNA and primers, triplex IS435A (SEQ ID NO.: 6) and triplex IS210B (SEQ ID NO.: 5).
[d]PCR amplificate prepared as described above using M.pt. genomic DNA and primers, M.pt.X (SEQ ID NO.: 7) and M.pt.Y (SEQ ID NO.: 8).

EXAMPLE 4

Sulforhodamine (Texas Red) may also be used as a sensitive reporter group to detect triple helices. In this example, PCR-amplified products were captured using Latex microparticles labelled with Triplex Probe A (SEQ ID NO.: 9) and detected with Sulforhodamine-labelled derivatives of Triplex Probe B (SEQ ID NO.: 10). Probe DNA was bound to sulforhodamine as follows. Probe DNA was transferred to 0.1M Borate buffer, pH 9.7, by PD-10 gel exclusion chromatography. 100 nmoles of oligonucleotide were reacted with 1 mg. of sulforhodamine (Molecular Probes Inc., Eugene, Oreg.) for 2 hrs. at 4° C. The labelled oligonucleotide was purified using a PD-10 column previously blocked with a 2% solution of bovine serum albumin (Sigma Co., St. Louis, Mo.) in 0.1M MES buffer, followed by equilibration with 0.1M MES buffer, pH 5.5.

M.pt. genomic DNA was PCR amplified using primers, triplex IS435A (SEQ ID NO.: 6) and triplex IS210B (SEQ ID NO.: 5) (producing PCR A=B). A 300 µl reaction mixture containing 30 µl of PCR amplificate, 30 µl of 5×FCA triple helix buffer (5×FCA Buffer; 1M MES, pH 5.5, 0.2% w/w sodium azide, 0.01M Spermine, 8% v/v Tween 20), 80 pmol of Sulforhodamine-labelled Probe B (SEQ ID NO.: 10), and 0.03% (w/v) Probe A (SEQ ID NO.: 9)-labelled Latex microparticles was incubated at room temperature. Aliquots were taken at the indicated time points and adsorbed onto an FCA plate held under vacuum. Following a 30 second vacuum step, the plates were washed once with 1×triple helix buffer, dried, and read in a fluorescence concentration analyzer (PANDEX Corp., Mundelein, Ill.) at an excitation wavelength of 590 nm and an emission wavelength of 620 nm. Results are shown in Table 7; values are expressed in relative fluorescence units.

TABLE 7

| Time of Reaction (min) | 0.5 | 1.0 | 5.0 | 15.0 |
|---|---|---|---|---|
| Fluorescence | 446 | 792 | 926 | 948 |

To test the specificity of triple helix formation, a 20 µl analytical mix containing 4 µl of 5×FCA Buffer was added to varying amounts of either a PCR A=B or M.pt. X=Y PCR amplificate. Samples were processed for FCA analysis as described above for Table 7. Results are shown in Table 8. The bottom line shows that the "worst case" signal to background ratio is 2.7:1.

TABLE 8

| PCR A = B (µl) | 0 µl | 1 µl | 3 µl | 5 µl |
|---|---|---|---|---|
| Fluorescence | 460 | 1916 | 5416 | 7444 |
| M.pt. X = Y (µl) | 0 µl | 1 µl | 3 µl | 5 µl |

TABLE 8-continued

| Fluorescence | — | 756 | 1762 | 2778 |
|---|---|---|---|---|
| Signal/Background | — | 2.5 | 3.1 | 2.7 |

EXAMPLE 5

Figure 3:
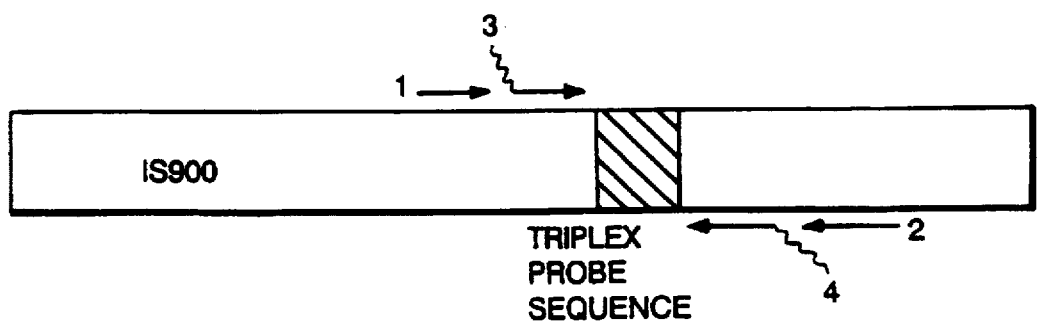
FIG. 3 is a schematic representation of the IS900 target sequence and the triple helix-forming primers and flanking primers used for PCR amplification.

The primary source of background signal and, as such, the component limiting detection sensitivity is the production of "primer dimers". In the examples above, such dimers form between triplex IS210B (SEQ ID NO.: 5) and triplex IS435A (SEQ ID NO.: 6). To increase detection sensitivity, target DNA was subjected to two rounds of PCR amplification: a first round using standard flanking primers and a second round using nested triple helix-forming primers as follows. "Triple helix-forming" primers (i.e., 3 and 4 of FIG. 3) were designed to amplify the region encompassed by nucleotides 843 to 1004. "Flanking primers" (i.e., 1 and 2 of FIG. 3) were designed to amplify sequences outside of and including the triple helix-forming primers, i.e., the region encompassed by nucleotides 854 to 106. In general, these primers may be of any sequence complementary to the genomic sequence and located outside the region amplified by the triple-helix forming primers.

Samples of IS900 sequence contained in the plasmid PMB22 were diluted in a series of six 10-fold steps. Flanking primers 1 (SEQ ID NO.: 11) and 2 (SEQ ID NO. 12), of sequence shown below, were used to amplify the IS900 sequence between them; this sequence included the binding sites for the triple helix-forming primers 3 (SEQ ID NO.: 13) and 4 (SEQ ID NO.: 14) of sequence shown below.

| 5' | gcccgcaacgccgatacc | 3' | IS900 Flanking primer 1 (SEQ ID NO.: 11) |
|---|---|---|---|
| 5' | cccaggatgacgccgaat | 3' | IS900 Flanking primer 2 (SEQ ID NO.: 12) |
| 5' | cccctttttctctccttttctcgccg ctaacgcccaacac | 3' | IS900 Nested triple helix-forming primer 3 (SEQ ID NO.: 13) |
| 5' | cctctcttctctcttctctcgct cctcgatcatcgc | 3' | IS900 Nested triplex helix-forming primer 4 (SEQ ID NO.: 14) |

Following 35 cycles of flanking primer (SEQ ID NO. 11 and 12) amplification (carried out as described above), 10 µl of the reaction mixture was amplified in a 90 µl PCR mix using the triple helix-forming primers 3 (SEQ ID NO.: 13) and 4 (SEQ ID NO.: 14) and another 15 cycles of amplification (1 cycle is 94° C. for 1 min, followed by 45° C. for 45 sec, followed by 72° C. for 45 sec). 6 µl of the final PCR amplificate was then mixed with 24 µl of standard Analytical Mix (2.4 µl of 2.5% Triplex probe A (SEQ ID NO. 9)-labelled Latex microparticles, i.e., approximately 100 pmoles Triplex probe A (SEQ ID NO.: 9) strand; 2.4 µl Sulforhodamine labelled-Triplex probe B (SEQ ID NO.: 10) of concentration 0.8–1.0 pmol/µl; 4.8 µl 5×Triple Helix Formation Buffer, i.e., 1M MES, 8% (v/v) Tween 20, 10 mM Spermine, 0.01% (w/v) sodium azide; 1.6 µl of 0.0025% (w/v) New Yellow-Orange flouresent microspheres; and 12.8 µl H$_2$O). The mixture was incubated at room temperature for 30 min and then transferred to an FCA plate, and the results were read using an excitation wavelength of 590 nm and emission wavelength of 620 nm.

Figure 4:
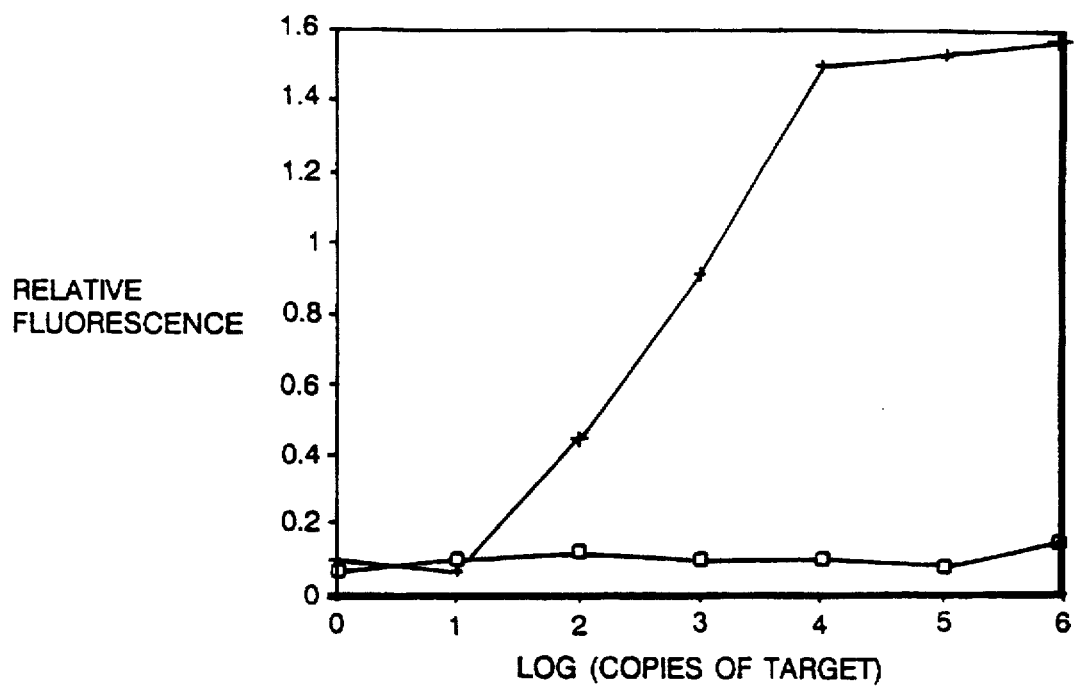
FIG. 4 is a graph showing triple helical detection of M. paratuberculosis-derived sequence IS900.

FIG. 4 shows that IS900 was selectively detected by FCA of the PCR amplificate generated with nested triple helix-forming primers 3 (SEQ ID NO. 13) and 4 (SEQ ID NO.: 14) and flanking primers, 1 (SEQ ID NO.: 11) and 2 (SEQ ID NO.: 12) (+). No significant detection of the IS900 sequence was observed in the PCR amplificate generated with flanking primers 1 (SEQ ID NO.: 11) and 2 (SEQ ID NO.: 12) alone (□).

EXAMPLE 6

In many cases, organisms contain endogenous sequences capable of forming triple helices with a single-stranded probe sequence. Feline immunodeficiency virus (FIV) contains such sequences (Talbott et al., Proc. Natl. Acad. Sci USA 86:5743, 1989). These sequences were used to design primers for PCR amplification and triplex probes for detection as follows.

Feline genomic DNA containing proviral copies of feline immunodeficiency virus was prepared from FIV-infected CRFK cells by the method of Blin and Stafford (Nucl. Acids Res. 3:2303, 1976). Triplex Primer A (SEQ ID NO.: 15), complementary to nucleotides 9003 to 9020, and Primer 2 (SEQ ID NO.: 16), complementary to nucleotides 8918 to 8935 were designed (as described above) using the published feline immunodeficiency virus sequence of Talbott et al. (above).

| 5' | cgaatcaaatcaaactaa cccctttttctctcctttc | 3' | Triplex Primer A (SEQ ID NO.: 15) |
| 5' | tctaactctgtcatcatc | 3' | Primer 2 (SEQ ID NO.: 16) |
| 5' | ttcttcttcttctttcttctt-NH$_2$ | 3' | Endogenous Triplex Probe P (SEQ ID NO.: 17) |

Figure 5:
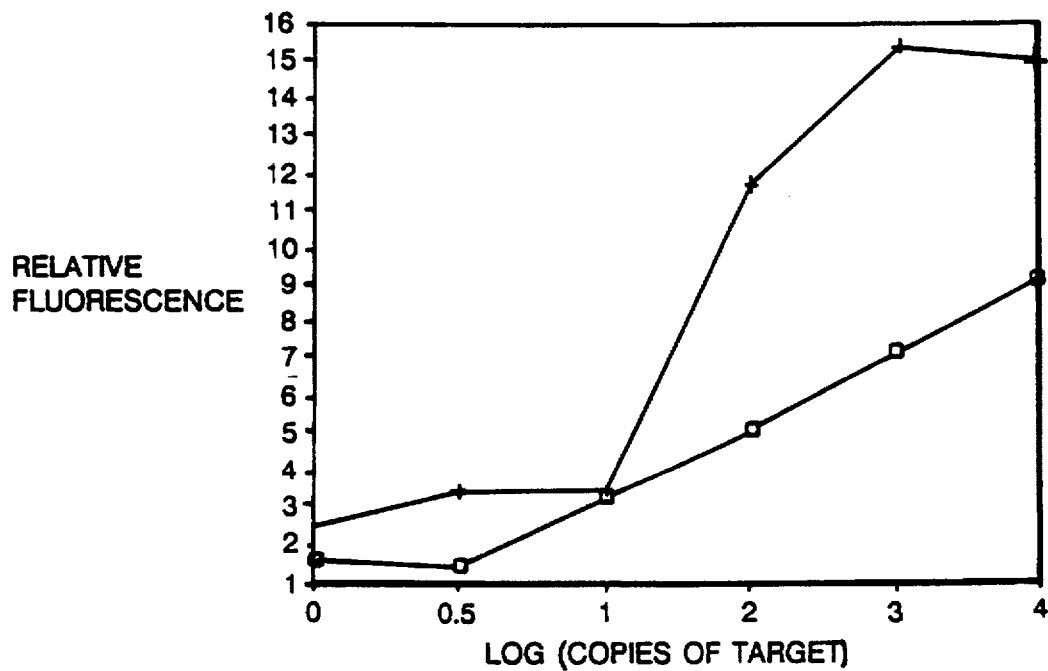
FIG. 5 is a graph showing detection of an endogenous triple helix-forming sequence of feline immunodeficiency virus.

Feline genomic DNA of concentration 0.5 μg/μl and including 5×10$^5$ copies of FIV provirus was subjected to PCR amplification (by the method described in Example 5) using Triplex Primer A (SEQ ID NO.: 15) and Primer 2 (SEQ ID NO.: 16). 6 μl of the resulting amplificate was mixed with 24 μl of Standard Analytical Mix containing Triplex Probe A (SEQ ID NO. 9)-labelled Latex microparticles and sulforhodamine labelled-Triplex probe P (SEQ ID NO.: 17). FIV sequences were detected in PCR amplificates which were generated using either 0.4 μM (□, FIG. 5) or 0.8 μM (+, FIG. 5) primer concentration. Results of these analyses are shown in FIG. 5. The endogenous FIV triple helix-forming sequence was selectively detected by Triplex Probe P (SEQ ID No.: 17) in this assay.

FIV contains a second putative triple helix-forming sequence (i.e., aaaaggaaaagacaaagaagaagaaagaaagaagaaa; nucleotides 8956-8992; SEQ ID NO.: 49). This sequence may be used to design PCR primers and a complementary triplex probe for detection of an FIV target sequence as described above.

EXAMPLE 7

To illustrate the generality of the methods of the invention, triple helix-forming primers and flanking primers were developed for detection of caprine encephalitis arthritis virus (CEAV) and human immunodeficiency virus 1 (HIV-1). Viral polymerase (pol) genes sequences, obtained from the Genbank database, were used to design the following primers for PCR amplification:

| 5' | taggaaaggcacccccacattgg 3' | CAEV Flanking primer 1 (SEQ ID NO.: 18) |
| 5' | cccctaagatctcctccatgg 3' | CAEV Flanking primer 2 (SEQ ID NO.: 19) |
| 5' | cccctttttctctcctttctcat taggacttccgcatccgg 3' | CAEV Nested triple helix-forming primer 3 (SEQ ID NO.: 20) |
| 5' | cctctcttctctcttctctcgca agtgtactctcgatatgg 3' | CAEV Nested triple helix forming primer 4 (SEQ ID NO.: 21) |

HIV-1:

| 5' | gcactttaaattttcccattagtcc 3' | HIV Flanking primer 1 (SEQ ID NO.: 22) |
| 5' | cctgcgggatgtggtattcc 3' | HIV Flanking primer 2 (SEQ ID NO.: 23) |
| 5' | cccctttttctctcctttctcaa gccaggaatggatggcc 3' | HIV Nested triple helix-forming primer 3 (SEQ ID NO.: 24) |
| 5' | cctctcttctctcttctctccag aagtcttgagttctcc 3' | HIV Nested triple helix-forming primer 4 (SEQ ID NO.: 25) |

Figure 6:
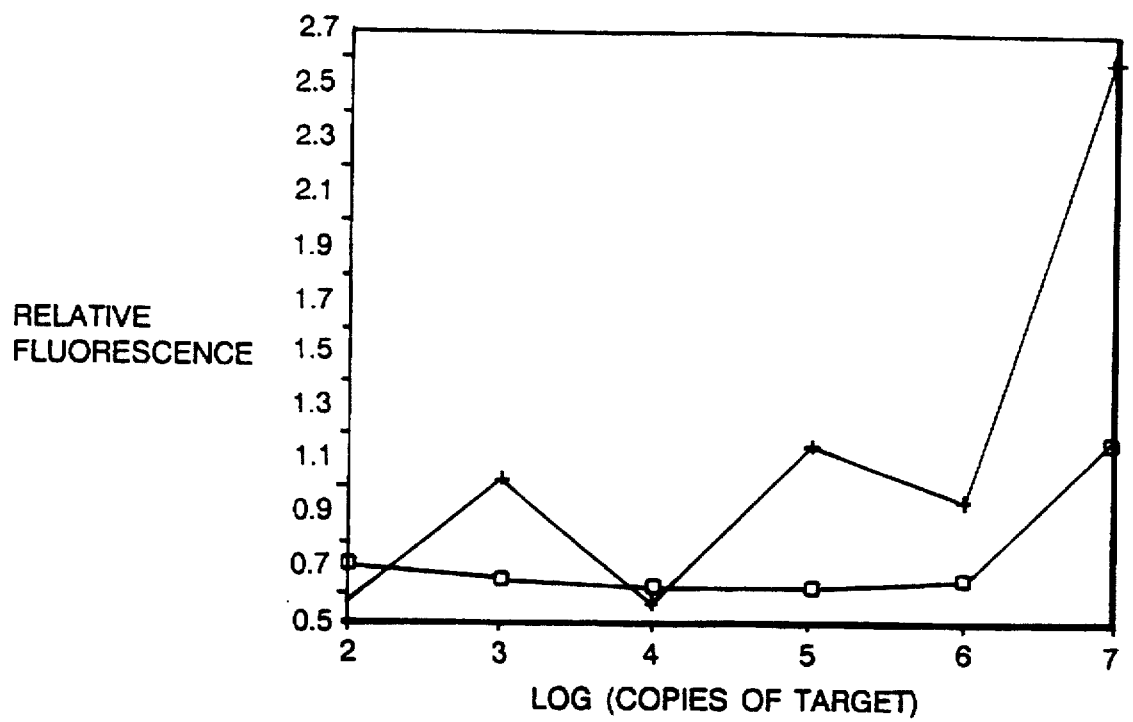
FIG. 6 is a graph showing triple helical detection of a caprine arthritis encephalitis virus-derived sequence.
Figure 7:
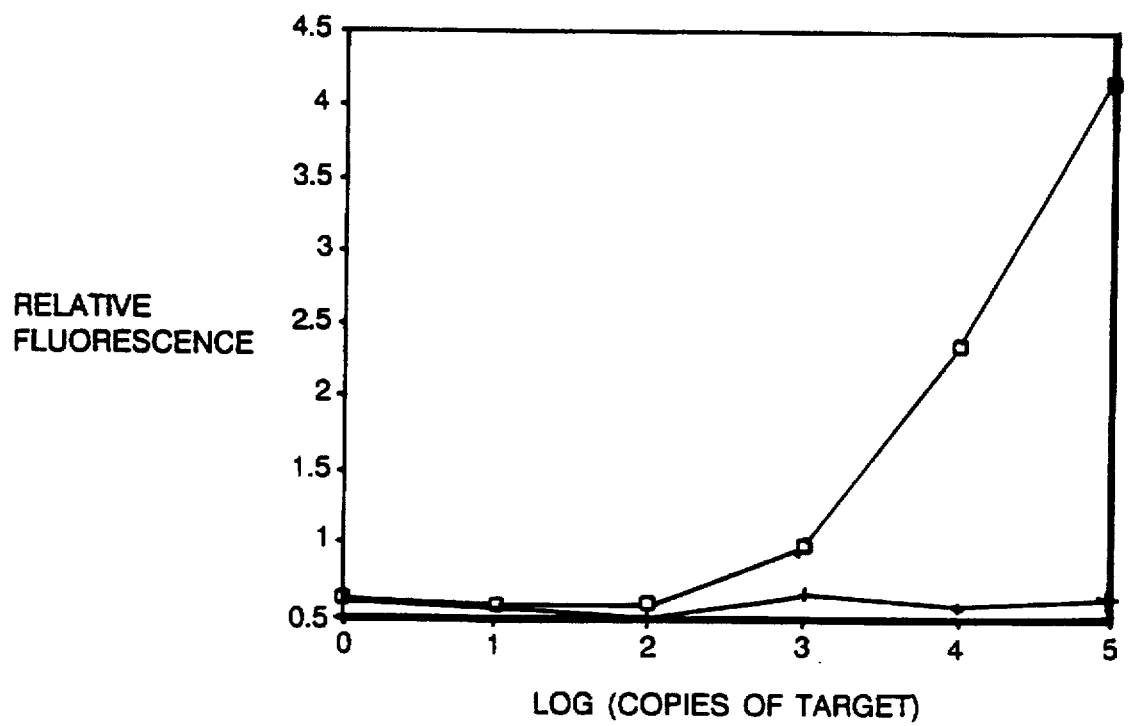
FIG. 7 is a graph showing triple helical detection of a human immunodeficiency virus, type 1-derived sequence.

CAEV DNA was obtained as a plasmid clone from the LCMB (National Institutes of Health, Laboratory of Cellular and Molecular Biology); recombinant clone collection (DNA #3041N); HIV-1 DNA was obtained from the American Type Culture Collection (Bethesda, Md.). DNA samples were subjected to PCR amplification (by the method described in Example 5), and the resulting amplificate probed with a third strand of DNA using a Standard Analytical Mix, also as described in Example 5. For both CAEV and HIV-1 assays, Probe A (SEQ ID NO.: 9)-labelled Latex microparticles and sulforhodamine labelled-Triplex probe B (SEQ ID NO.: 10) were used for detection. Results of these analyses are shown in FIG. 6 (CAEV) and FIG. 7 (HIV-1). CAEV (+, FIG. 6) and HIV-1 (□, FIG. 7) target sequences were detected in each case by this assay using nested triple helix-forming primers and flanking primers. No significant detection was observed using only flanking primers (□, FIG. 6; +, FIG. 7).

EXAMPLE 8

The procedure described in Example 6 could also be used to test for the presence of the organisms: human immunodeficiency virus, type 1 (HIV-1), feline leukemia virus (FELV), human papilloma virus-16 (HPV-16), human papilloma virus-18 (HPV-18), and hepatitis B virus (HBV). The genomic sequence of each of these organisms includes an endogenous sequence(s) predicted to form a triple helical structure. Such sequences include the following (5' to 3'):

HIV-1
aggggaaagaaaaaa (nucleotides 404-419; SEQ ID NO.: 26);
aaatggaaaaggaagggaaaa (nucleotides 2250-2270; SEQ ID NO.: 27);

FELV
aagggaaaaaggaaa (nucleotides 1927-1941; SEQ ID NO.: 28);
aaaagggagacccagaggaaagggaagaaaga (nucleotides 2147-2179; SEQ ID NO.: 29);

HPV-16
agaggaggaggatgaaatagatgg (nucleotides 657-680; SEQ ID NO.: 30);
ggggaagaggg (nucleotides 889-899; SEQ ID NO.: 31);

HPV-18
aaaaatagatgaaggggaga (nucleotides 2227-2247; SEQ ID NO.: 32);
gaggaagaggaaga (nucleotides 2804-2817; SEQ ID NO.: 33);

HBV
tccccttcttcttctgccgttcc (nucleotides 1490-1512; SEQ ID NO.: 34);
ctccctccttcctc (nucleotides 2508-2522; SEQ ID NO.: 35).

Following amplification of the triple helix-forming target sequence (by the methods described in the above examples), a triplex probe which includes a sequence complementary to the duplex PCR product would be used to detect the presence of the organism. For example, an HIV-1 triplex probe may include the sequence complementary to nucleotides 404-419 of HIV-1 (i.e., tcccctttcttttt-NH$_2$; SEQ ID NO.: 36).

Other Embodiments

Other embodiments are within the following claims. For example, any target sequence containing a triple helix-forming sequence (either naturally or as a result of some amplification process) may be detected by these methods. The target sequence may be DNA or RNA. Detection may be accomplished by any reporter group, for example, any detectable fluorescent, enzymatic, radioactive, chemiluminescent, or bioluminescent reporter group. Alternatively, aggregation-based, mass-based, interference-based or absorption-based reporter groups may be used to capture and/or detect triple helical product. Capture and/or detection of these reporter groups is well known to those skilled in the art.

The methods of the invention may be carried out using assay formats other than a microtiter well or an FCA plate. For example, mass-based surface acoustic wave or surface transverse wave techniques, fluorescence analysis using fiber optic wave guides, evanescent zone analysis, or any other format which allows detection of the triple helical product may be used. Moreover, the process may be automated, for example, by using a PCFIA plate format.

As described above, detection of target sequences is accomplished using triple helix probes that permit capture and detection. Capture and detection may be accomplished by separate probe molecules, each hybridizing at a different site (i.e., a capture probe and a detection probe), in which case the "third strand" of the invention includes two separate meolecules. Alternatively, both these functions may be achieved with a single triplex probe. In one particular example, a single probe is bound at one end to a Latex microparticle (for capture) and at the other end to sulforhodamine (for detection). In addition, we have shown that triple helix formation increases the ultraviolet fluorescence of ethidium bromide intercalated into the duplex target sequence. When triple helical formation is assayed as an increase in ethidium bromide fluorescence, there is no need to covalently bind a reporter molecule to a triplex probe.

Triple helix formation may also be measured by a competitive binding assay. In one example, product duplexes (generated as described above) containing a triple helix-forming region are hybridized to a third strand triplex probe to which is covalently bound a detectable label, e.g., sulforhodamine. To the hybridization mixture is then added a single-stranded or double-stranded "hook" sequence to which is covalently bound a solid support, e.g., a Latex microparticle. The hook sequence is complementary to the labelled third strand triplex probe. Triplex probe sequences which bind to the solid support-bound hook sequence (i.e., those third strands which are in excess following hybridization with product duplexes) are isolated (e.g., on an FCA plate following vacuum filtration or by centrifugation) and assayed (e.g., by measuring sulforhodamine fluorescence). The presence and/or concentration of product duplexes is inversely proportional to the quantity of label detected. Such capture of excess triplex probe by hook sequence is facilitated by triple helical, e.g., Hoogsteen, interactions in the case of the double-stranded hook and double helical, e.g., Watson-Crick, interactions in the case of the single-stranded hook sequences.

The methods of the invention allow detection of any target sequence (i.e., from any organism) whose sequence, or a portion thereof, has been determined. For example, pathogenic organisms, including, but not limited to, retroviruses (e.g., human immunodeficiency virus-1, feline leukemia virus, feline immunodeficiency virus), hepatitis virus, bovine viral diarrhea virus, and papilloma viruses (e.g., human papilloma viruses, type 16 and type 18) may be detected by designing appropriate triplex primers and probes (based on published sequences) and assaying for such sequences as described above.

FIG. 8 is a list of genes which include putative endogenous triple helix-forming sequences. The genes were obtained from the GENBANK database based upon their possession of a perfect 25 base pair homopolymer region. The first column lists the GENBANK Accession Code, and the second column lists the full name of the gene and the organism from which it derives. Using this approach, other homopolymer-containing genes may be identified; accessing the full sequence of such genes would allow the exact homopolymer sequences and their positions within the genes to be determined. FIG. 8 demonstrates that homopolymer tracts, i.e., endogenous triple helix-forming sequences, are resident in the genome of a variety of organisms and provide candidate sequences for detection by the methods of this invention.

I claim:
1. A method of determining whether a sample contains a target nucleic acid, said method comprising the steps of:
   (a) amplifying said target nucleic acid in vitro, by performing cycles of denaturation and replication using at least one nucleic acid reagent, to yield an amplified population of product duplexes comprising nucleotide sequence from said target nucleic acid, said product duplexes comprising a triple helix-forming sequence of nucleotide base pairs, and,
   (b) thereafter, while at least some of the nucleic acid reagent used in the amplifying step remains mixed with said amplified population, combining said population with a single-stranded nucleic acid probe (third strand) under conditions to allow specific binding of said probe to said product duplexes to form said triple helix, in that the nucleic acid reagents do not specifically bind to said product duplexes, said probe being characterized in that:
   i. the probe comprises a sequence of nucleotides which is long enough to form a triple helix by specifically binding to said triple helix-forming sequence of said product duplexes at a site that at least partially overlaps with a site corresponding to the sequence of said nucleic acid reagent, and, ii. components of the probe in addition to said nucleotide sequence, if any, allow said nucleotide sequence to form a triple helix with said product duplexes under said conditions; and (c) detecting the presence of said triple helix directly as indicative of the presence of said target nucleic acid in said sample.

2. The method of claim 1, wherein said amplifying is accomplished by polymerase chain reaction.

3. The method of claim 2, wherein said polymerase chain reaction is accomplished using at least two PCR primers, the first of said PCR primers being a nucleic acid comprising (1) a first region which is complementary to one strand of said target nucleic acid, and (2) a second region comprising a sequence of at least 15 nucleotides which, when incorporated into said product duplex, is capable of forming a triple helix; the second of said PCR primers being a nucleic acid which comprises a nucleotide sequence that is complementary to the second strand of said target nucleic acid.

4. The method of claim 1, wherein said amplifying is accomplished by ligase chain reaction.

5. The method of claim 4, wherein said ligase chain reaction is accomplished using two or more pairs of LCR hybridization probes, wherein one said probe of each pair comprises a nucleic acid which is complementary to said target nucleic acid, and the second said probe of each pair being a nucleic acid comprising (1) a first region which is complementary to an adjacent segment of said target nucleic acid, and (2) a second region comprising at least 15 nucleotides which, when incorporated into said product duplex, is capable of forming a triple helix.

6. The method of claim 1, wherein said third strand of nucleic acid comprises a polypyrimidine of at least 15 nucleotides.

7. The method of claim 6, wherein said third strand of nucleic acid further comprises one or more purine residues, wherein each said purine residue is flanked by 9 or more pyrimidine residues.

8. The method of claim 1, wherein said third strand of nucleic acid comprises a polypurine of at least 15 nucleotides.

9. The method of claim 8, wherein said third strand of nucleic acid further comprises one or more pyrimidine residues, wherein each said pyrimidine residue is flanked by 9 or more purine residues.

10. The method of claim 7, wherein said polypyrimidine comprises one or more protonated, methylated, or halogenated nucleotides.

11. The method of claim 1, wherein said third strand of nucleic acid is covalently attached to a solid support.

12. The method of claim 11, wherein said solid support is a microparticle.

13. The method of claim 1 wherein said target nucleic acid is detected using an fluorescence concentration assay format.

14. The method of claim 1 wherein said target nucleic acid is detected using a particle concentrated fluorescence immunoassay format.

15. The method of claim 1, wherein said nucleic acid is detected using a microtiter well format.

16. The method of claim 1, wherein said third strand of nucleic acid is covalently attached to a reporter group.

17. The method of claim 16, wherein said reporter group is sulforhodamine.

18. The method of claim 16, wherein said reporter group is alkaline phosphatase.

19. The method of claim 1, wherein said nucleic acid is detected by enhanced ethidium bromide fluorescence following contact with said third strand of nucleic acid.

20. The method of claim 1, further comprising isolating said duplex prior to detecting said duplex.

21. The method of claim 1, further comprising detecting a second target nucleic acid in said sample, wherein said second nucleic acid comprises a second triple helix-forming sequence, said second triple helix-forming sequence being least 15 nucleotide base pairs in length;

said second triple helix-forming sequence specifically forming a triple helix with: a) a single strand of nucleic acid other than said first single strand and b) not with said first strand.

22. The method of claim 21, wherein said detection of said second nucleic acid, different from said product duplexes, is by a method comprising specifically binding the triple helix-forming sequence of said second nucleic acid to a third strand of nucleic acid without denaturation of said duplex.

23. The method of claim 1, wherein said nucleic acid is derived from *M. paratuberculosis*.

24. The method of claim 1, wherein said nucleic acid is derived from a retrovirus.

25. The method of claim 24, wherein said retrovirus is a human immunodeficiency virus.

26. The method of claim 25, wherein said third strand of nucleic acid comprises at least 15 consecutive nucleotides of the sequence: tcccccttttctttttt (SEQ ID No.: 37).

27. The method of claim 25, wherein said third strand of nucleic acid comprises at least 15 consecutive nucleotides of the sequence: tttaccttttccttcccttt (SEQ ID NO.: 38).

28. The method of claim 24, wherein said retrovirus is a feline leukemia virus.

29. The method of claim 28, wherein said third strand of nucleic acid comprises the sequence: ttccctttttccttt (SEQ ID NO.: 39).

30. The method of claim 28, wherein said third strand of nucleic acid comprises at least 15 consecutive nucleotides of the sequence: ttttcccctctgggggtctccttcccttctttct (SEQ ID NO.: 40).

31. The method of claim 24, wherein said retrovirus is a feline immunodeficiency virus.

32. The method of claim 31, wherein said third strand of nucleic acid comprises at least 15 consecutive nucleotides of the sequence: ttcttcttcttcttcttctt (SEQ ID NO.: 41).

33. The method of claim 31, wherein said third strand of nucleic acid comprises at least 15 consecutive nucleotides of the sequence: ttttccttttctgtttcttcttcttcttcttcttctt (SEQ ID NO.: 42).

34. The method of claim 1, wherein said nucleic acid is derived from a human papilloma virus.

35. The method of claim 34, wherein said human papilloma virus is HP-16.

36. The method of claim 35, wherein said third strand of nucleic acid comprises the sequence: cccttctccc (SEQ ID NO.:43).

37. The method of claim 35, wherein said third strand of nucleic acid comprises at least 15 consecutive nucleotides of the sequence: tctcctcctcctactttatctacc (SEQ ID NO.: 44).

38. The method of claim 34, wherein said human papilloma virus is HP-18.

39. The method of claim 38, wherein said third strand of nucleic acid comprises at least 15 consecutive nucleotides of the sequence: ttttatctacttcccctct (SEQ ID NO.: 45).

40. The method of claim 38, wherein said third strand of nucleic acid comprises the sequence: ctccttctccttct (SEQ ID NO.: 46).

41. The method of claim 24, wherein said retrovirus is a caprine arthritis encephalitis virus.

42. The method of claim 1, wherein said nucleic acid is derived from a hepatitis B virus.

43. The method of claim 42, wherein said third strand of nucleic acid comprises at least 15 consecutive nucleotides of the sequence: aggggaagaagaagacggcaagg (SEQ ID NO.: 47).

44. The method of claim 42, wherein said third strand of nucleic acid comprises the sequence: gagggaggaaaggag (SEQ ID NO.: 48).

45. The method of claim 8, wherein said polypurine comprises one or more protonated, methylated or halogenated nucleotides.

46. The method of claim 1, wherein said triple helix-forming product duplexes each comprise a first region that is homologous to said target nucleic acid, and a second region that is not naturally associated with said target nucleic acid, said second region being capable of forming a triple helix with a third strand of nucleic acid.

47. The method of claim 26, wherein said third strand of nucleic acid includes the sequence: tcccccttttctttttt (SEQ ID NO: 37).

48. The method of claim 27, wherein said third strand of nucleic acid includes the sequence: tttaccttttccttcccttt (SEQ ID NO: 38).

49. The method of claim 29, wherein said third strand of nucleic acid includes the sequence: ttcccttttccttt (SEQ ID NO: 39).

50. The method of claim 30, wherein said third strand of nucleic acid includes the sequence: ttttccctctggggtctcctttc-ccttctttct (SEQ ID NO: 40).

51. The method of claim 32, wherein said third strand of nucleic acid includes the sequence: ttcttcttcttctttcttctt (SEQ ID NO: 41).

52. The method of claim 33, wherein said third strand of nucleic acid includes the sequence: ttttccttttctgtttcttct-tctttctttcttcttt (SEQ ID NO: 42).

53. The method of claim 36, wherein said third strand of nucleic acid includes the sequence: cccttctccc (SEQ ID NO: 43).

54. The method of claim 37, wherein said third strand of nucleic acid includes the sequence: tctcctcctcctactttatctacc (SEQ ID NO: 44).

55. The method of claim 39, wherein said third strand of nucleic acid includes the sequence: tttttatctacttccccctct (SEQ ID NO: 45).

56. The method of claim 40, wherein said third strand of nucleic acid includes the sequence: ctccttctccttct (SEQ ID NO: 46).

57. The method of claim 43, wherein said third strand of nucleic acid includes the sequence: aggggaagaagaagacg-gcaagg (SEQ ID NO: 47).

58. The method of claim 44, wherein said third strand of nucleic acid includes the sequence: gagggaggaaaggag (SEQ ID NO: 48).

59. The method of claim 24, wherein said third strand of nucleic acid includes the sequence: ctctttcctctctttttcccc (SEQ ID NO: 9).

60. The method of claim 24, wherein said third strand of nucleic acid includes the sequence: ctctcttctctcttctctcc (SEQ ID NO: 10).

* * * * *